United States Patent [19]

Khawli et al.

[11] Patent Number: 5,990,286
[45] Date of Patent: Nov. 23, 1999

[54] ANTIBODIES WITH REDUCED NET POSITIVE CHARGE

[75] Inventors: Leslie A. Khawli, Arcadia; Alan L. Epstein, La Canada, both of Calif.

[73] Assignee: Techniclone, Inc., Tustin, Calif.

[21] Appl. No.: 08/781,449

[22] Filed: Jan. 10, 1997

Related U.S. Application Data

[60] Provisional application No. 60/037,187, Dec. 18, 1996.

[51] Int. Cl.$^6$ .......................... A61K 39/395; C07K 16/00
[52] U.S. Cl. ..................................... 530/387.1; 530/388.1; 530/389.1; 530/391.3; 530/391.7; 530/402
[58] Field of Search ................................ 530/402, 387.1, 530/388.1, 389.1, 391.3, 391.7

[56] References Cited

U.S. PATENT DOCUMENTS 5,021,571   6/1991   Mease et al. .

FOREIGN PATENT DOCUMENTS

| WO88/07553 | 10/1988 | WIPO . |
| WO89/12458 | 6/1989  | WIPO . |
| WO89/12458 | 12/1989 | WIPO . |
| WO90/09196 | 2/1990  | WIPO . |
| WO90/09196 | 8/1990  | WIPO . |
| WO91/07991 | 6/1991  | WIPO . |
| WO92/04052 | 3/1992  | WIPO . |

OTHER PUBLICATIONS

Frankel, Arthur E.; Immunotoxins, 1988 Kluwer Academic Publishers; Antibody–toxin conjugation; pp. 213–251.

Orlandi, Rosaria, et al; Hybridoma, vol. 5, No. 1, 1986; Change in Binding Reactivity of an Anti–Tumor Monoclonal Antibody After the Introduction of 2–Pyridyl Disulphide Groups; pp. 1–8.

Frankel, Arthur E.; Immuntoxins; 1988; Antibody–toxin conjugation; pp. 213–251.

Khawli, et al.; Antibody, Immunoconjugates, and Radiopharmaceuticals; vol. 6, No. 1, 1993; Improved Immunotargeting of Tumors with Biotinylated Monoclonal Antibodies and Radiolabeled Streptavidin; pp. 13–27.

Najafi, et al.; Nucl.Med.Biol., vol. 19, No. 2, The Evaluation of $^{186}$Re–labeled Antibodies Using $N_2S^4$ Chelate In Vitro and In Vivo Using Tumor–bearing Nude Mice; pp. 205–212.

Alauddin, et al.; Antibody, Immunoconjugates, and Radiopharmaceuticals; vol. 4, No. 3, 1991; Evaluation of $^{99m}$Tc–Labeled $N_2S_4$ Coupled B72.3 and Lym–1 Antibodies as Tumor–Imaging Agents in Tumor–Bearing Nude Mice.

Yazynin, et al., Immunology Letters; 41 (1994) pp. 235–239; Group–selective immunoassay.

Thakur, et al.; The Journal of Nuclear Medicine; vol. 35, No. 5, May 1994; Laboratory Studies; Technetium–99m–Labeled Monoclonal Antibodies: Influence of Technetium–99 Binding Sites; pp. 876–881.

Khawli, et al.; Cancer Biotherapy & Radiopharmaceuticals; vol. 11, No. 3, 1996; Improved Tumor Localization and Radioimaging with Chemically Modified Monoclonal Antibodies; pp. 203–215.

Ponomareva et al Immunologiga, 0(4) 1989 pp. 76–78. (Russian) abstract enclosed.

*Primary Examiner*—Paula K. Hutzell
*Assistant Examiner*—Geetha P. Bansal
*Attorney, Agent, or Firm*—Knobbe, Martens Olson & Bear, LLP

[57] ABSTRACT

Modified antibodies which have been by chemical conjugation with agents reactive with free amino groups are disclosed. Among the chemical agents disclosed for use in connection with the invention are heterobifunctional reagents and biotin. The use of these modified antibodies in the diagnosis and therapy of cancer and other mammalian disease is also disclosed. Diagnostic uses include immunoscintography. The modified antibodies may be further conjugated with labels or biologically active molecules for use in diagnosis and therapy. The modified antibodies may also be formulated into pharmaceutical compositions for these purposes.

11 Claims, 22 Drawing Sheets

Image obtained on day 7 after injection of I-131 labeled intact Lym-1.
Region 1, whole mouse; Region 2, Raji tumor Image obtained on day 7 after injection of
I-131 labeled modified Lym-1.
Region 1, whole mouse; Region 2, Raji tumor Image obtained on day 7 after injection of I-131 labeled modified Lym-1.
Region 1, whole mouse; Region 2, Raji tumor Image obtained on day 5 after injection of I-131 labeled modified Lym-1.
Region 1, whole mouse; Region 2, Raji tumor Image obtained on day 1 after injection of I-131 labeled modified B72.3.
Region 1, whole mouse; Region 2, LS174T tumor Image obtained on day 4 after injection of I-131 labeled modified B72.3.
Region 1, whole mouse; Region 2, LS174T tumor

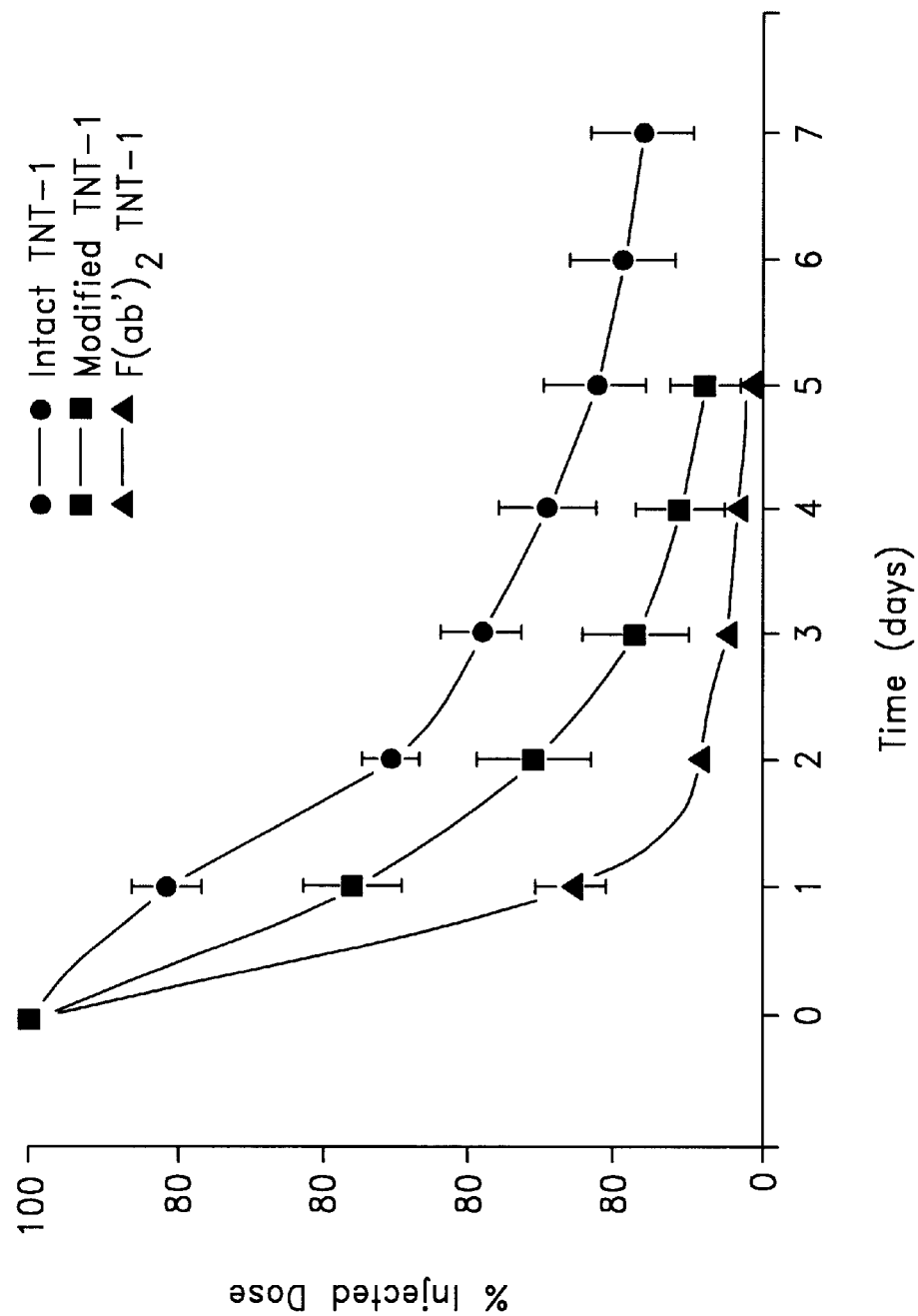

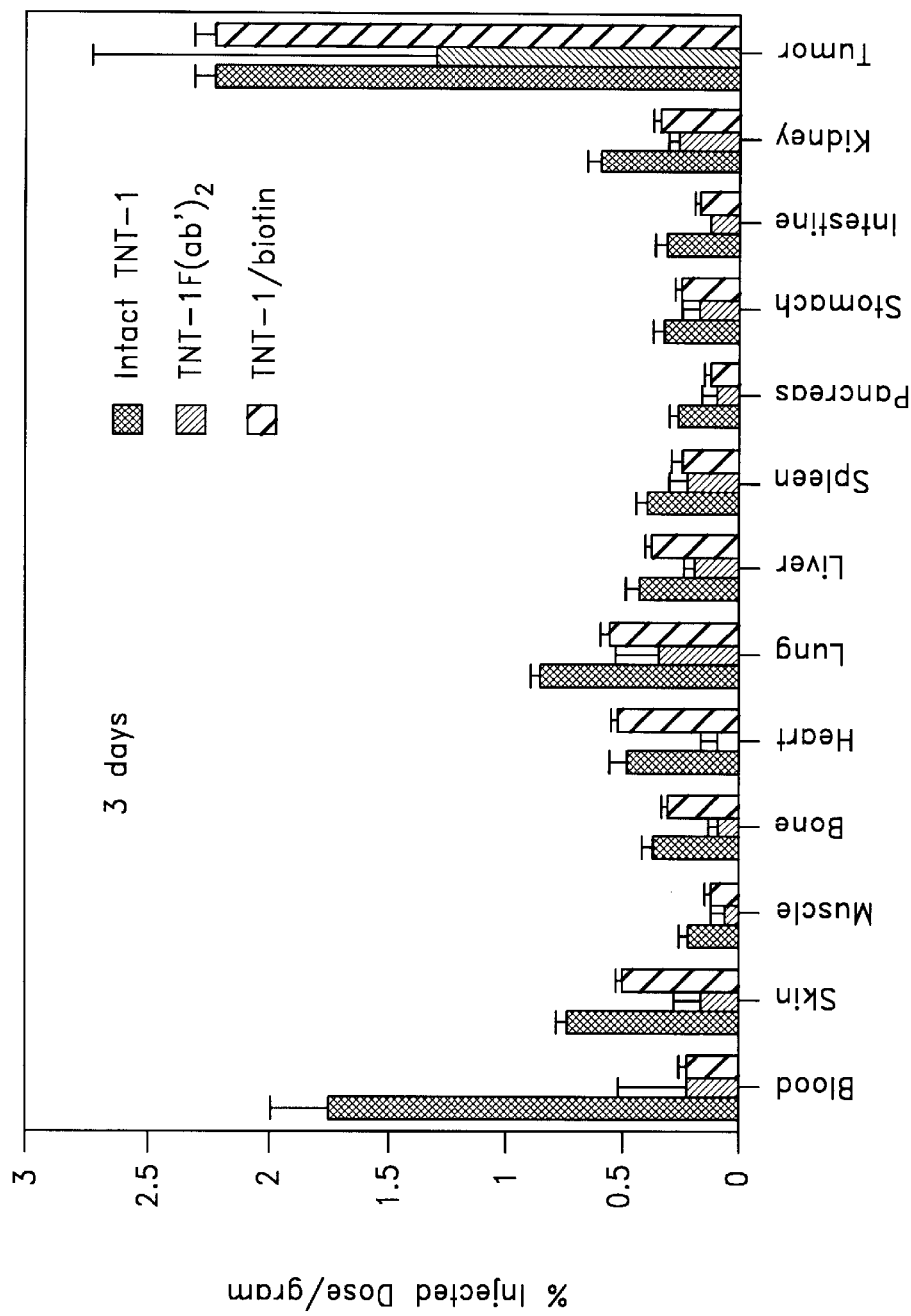

ANTIBODIES WITH REDUCED NET POSITIVE CHARGE

RELATED APPLICATION

This application claims the benefit of priority under 35 U.S.C. § 119(e) of the U.S. patent application having Ser. No. 08/586,075 originally filed as a nonprovisional application Jan. 11, 1996, and converted to a provisional application by petition filed Dec. 18, 1996, and assigned provisional Application No. 60/037,187.

BACKGROUND OF THE INVENTION

1. Field of the Invention

The present invention relates generally to the field of modified antibodies. More specifically, the invention relates to chemically modified antibodies having increased binding specificity, improved pharmacokinetics and localization capabilities. These modified antibodies are particularly useful in the diagnosis and therapy of cancer and other mammalian disease.

2. Description of the Prior Art

The use of antibodies, particularly monoclonal antibodies ("MAb's"), has the potential to be an extremely valuable approach in the diagnosis and treatment of cancer. An important property of MAb's is their specificity for single antigens.

MAb's specific to tumor cell antigens have been produced. It has also been shown that MAb's may be efficiently coupled to adjuncts such as radionuclides. Such radiolabelled MAb's are useful in providing clinical data, such as tumor imaging from immunoscintography, also known as g-camera imaging or radioimmunoimaging. In immunoscintography, the MAb's are allowed to bind to the specific tissue or tumor types having the antigen recognized by the MAb's. The radionuclides are then visualized through the use of appropriate technology, such as through the use of a germanium camera. It is the unique specificity of MAb's which enables their application in immunoscintography of tumors and other types of tissues.

However, the use of MAb's in immunoscintography has been limited due to high background levels and low binding capacity of the MAb's to their antigens. Experimental studies suggest that the biodistribution of radio-labelled MAb's is dependent on many factors, including the specificity and clearance time of the antibody. For effective diagnosis of a tumor through immunoscintography, an antibody should be selected which binds to an antigen which is dense and homogeneous on the tumor cell surface. Effective diagnosis through immunoscintography also requires that the antibody chosen should effectively bind to the tumor antigen. However, often MAb's which bind to appropriate antigens do not offer the required high binding affinity. Additionally, even the use of those MAb's which bind with high affinity relative to other MAb's may still produce a high level of non-specific binding, resulting in high background levels when used in immunoscintography. Thus, there is a need for a method of improving the effectiveness of binding of MAb's in order to improve immunoscintography as a diagnostic tool.

Additionally, the cytotoxic effect of MAb's can be markedly increased by coupling to radionuclides, drugs or toxins. The unique specificity of MAb's has raised hopes of the development of immunotherapy. In immunotherapy, biologically active agents are delivered using MAb's to particular undesirable cell types, such as tumor cells, thereby affecting the undesirable cell types without affecting other cells of the subject. However, immunotherapies require extremely high specificity antibodies in order to avoid affecting healthy tissue. Thus, a method of increasing the specificity of MAb's would be highly beneficial in achieving the goal of a safe, effective immunotherapy.

Many MAb's remain in the circulation for several days following introduction into a subject. This is undesirable for at least two reasons. One reason is that circulating MAb's produce high background levels in immunoscintography. A second reason is that circulating MAb's coupled to radionuclides or other potentially cytotoxic agents may produce undesirable side effects in the subject after prolonged exposure. Thus, there is a need for a method of decreasing the clearance time of MAb's. Of course, too great a decrease would result in MAb's being eliminated before any effective use of the MAb's could be made. Thus, there is a particular need for a method of decreasing the clearance time of MAb's without substantially affecting uptake of MAb's by tumor or other target tissue.

One factor which is critical in determining both the specificity and clearance time of an antibody is the form of the antibody. As used herein, an "intact" antibody molecule will refer to an unmodified antibody molecule comprised of two heavy chains and two light chains. The intact, whole antibody molecule is seen on the reactant side of the chemical equation of FIG. 1. As seen in FIG. 1, the intact molecule is divided into the $F_c$ and the $F_{ab}$ domains. $F(ab')_2$, the bivalent form of the $F_{ab}$ fragmnent, may be produced through the digestion of the $F_c$ domain with a protease.

The two heavy chains (designated as "H" in FIG. 1) are held together by one or more disulfide bridges. In intact molecules these disulfide bridges are normally protected from reducing agents. It has been found however, that removal of the $F_c$ domain allows facile reduction of the disulfide bridges. Thus, F(ab'), the monovalent form, may be produced from $F(ab')_2$ through the action of a mild reducing agent. Parham, P., On the Fragmentation of Monoclonal IgG1, IgG2a, and IgG2b from BALB/c Mice, *J Immunol.* 131: 2895 (1983), the disclosure of which is hereby incorporated by reference, describes a method for the production of F(ab') and $F(ab')_2$. A schematic representation of the changes believed to occur in this method is shown by the chemical equation of FIG. 1.

$F_c$ has been found to be responsible for much of the non-specific binding of antibody molecules. It is also believed that the molecular weight of the fragments is below the threshold for glomerular filtration, thus allowing for rapid elimination of the fragments. Therefore, one approach to increasing clearance time of antibodies for use in radio-imaging has been to break down intact antibody into various fragments, such as Fab and its divalent form, $F(ab')_2$. As expected, these fragments are cleared from the body so rapidly that their utility is reduced. Moreover, these fragments may result in reduced uptake by tumor or other target tissue relative to intact antibody. Thus, although the use of these fragments in immunoscintography may provide better clearance and a higher target tissue to background ratio than with intact MAb's, the absolute concentration of MAb's in the target tissue containing the antigen to which the MAb's will bind has been found to be up to three times or more as much with intact MAb's as with either of the fragments. Furthermore, both types of fragments are removed from the blood stream very rapidly. Accordingly, the time of effectiveness for diagnostic or therapeutic techniques using these fragments is very short.

Heterobifunctional reagents are reagents having two groups capable of participating in different reactions. For example, succinimidyl 3-(2-pyridyldithio)-propionate (SPDP) is heterobifunctional in that its N-hydroxysuccinimide ester group reacts with amino groups and the 2-pyridyl disulphide structure reacts with aliphatic thiols.

Orlandi et al., Change in Binding Reactivity of an Anti-Tumor Monoclonal Antibody After the Introduction of 2-Pyridyl Disulphide Groups, *Hybridoma* 5:1–8 (1986), reported that an increase in the in vitro binding of MAb's raised against human ovarian carcinoma could be obtained after chemical conjugation with the heterobifunctional reagent, SPDP.

The conjugated MAb's used by Orlandi et al. had on average, 11 PDP groups per molecule. Orlandi et al. found that the modified MAb's increase their binding activity in vitro to an extent that molecules not detected by the unmodified MAb's can be detected. These researchers reported no studies of the use of the conjugated MAb's in vivo. Additionally, these researchers believed that molecules having a very low number of antigenic sites were detected by the conjugated MAb's. Accordingly, the PDP modified MAb's had greatly reduced target-cell specificity relative to the unmodified counterparts.

Thus, despite the above advances, there remains a need for modified antibody fragments exhibiting greater specific activity to tumor antigens, allowing more absolute concentration of antibody to accumulate in tumor, and also having relatively rapid clearance time from the blood pool, yet not so rapid as to reduce therapeutic or diagnostic effectiveness.

BRIEF DESCRIPTION OF THE FIGURES

FIG. 16 shows the whole body retention of different preparations of radiolabeled MAb's TNT-1 in athymic nude mice.

FIGS. 17A–D show a series of bar graphs. FIGS. 17A and 17C represent the percentage of injected intact TNT-1 and biotinylated TNT-1 localizing to tumor and various tissues. FIGS. 17B and 17D represent ratios of labeled antibodies localizing to tumor and various organs.

SUMMARY OF THE INVENTION

Figure 1:
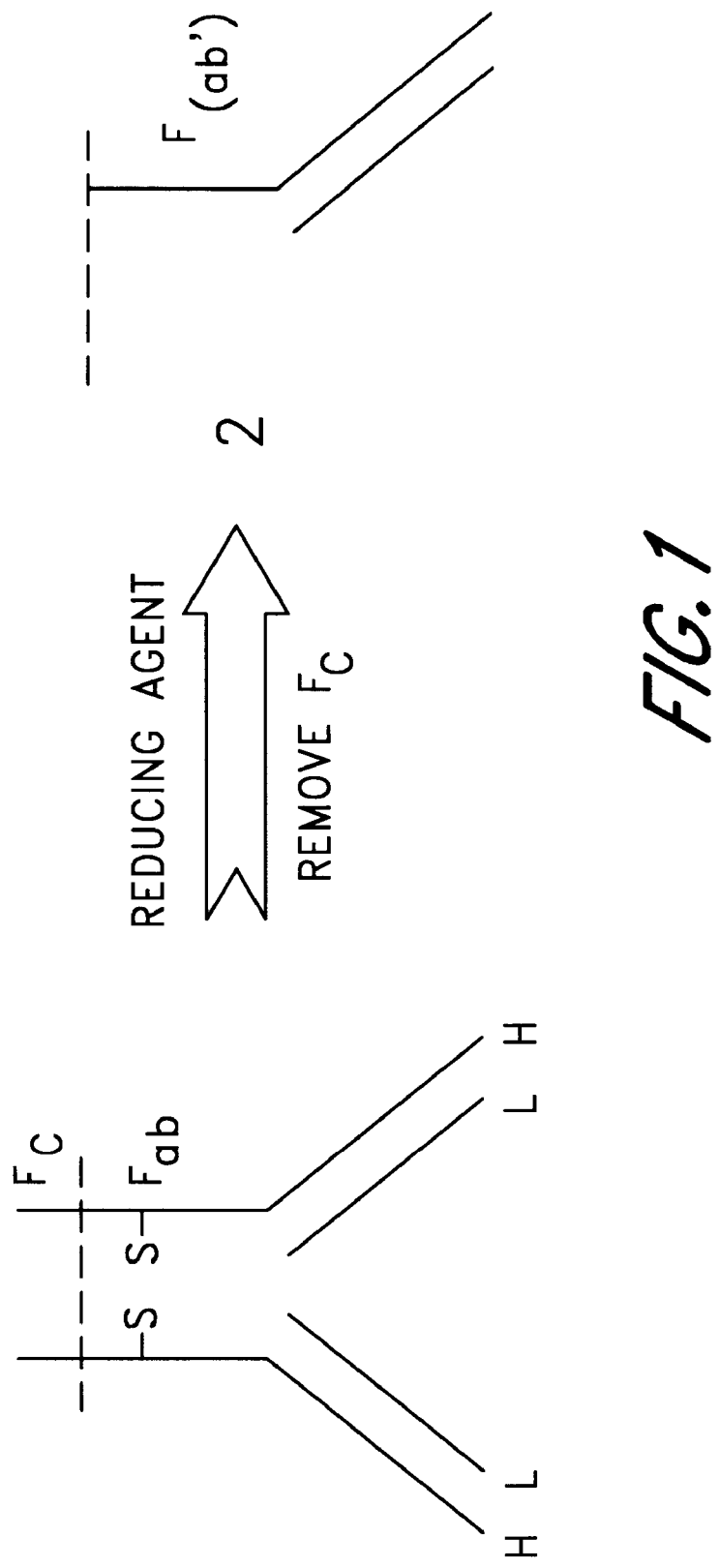
FIG. 1 shows a schematic representation of the changes believed to occur in a method of producing F(ab') and F(ab')$_2$ fragments.

One aspect of the present invention relates to an antibody conjugated to a chemical reagent at at least one of a plurality of free amino groups disposed on the antibody to produce a modified antibody. The antibody has a reduced net positive charge compared to intact antibody. The antibody also has an in vivo clearance rate between the clearance rates of F(ab')$_2$ fragments and intact antibodies of the same type. In the antibodies in this aspect of the invention, the chemical reagent is not a heterobifunctional agent. The antibodies also include a chemical moiety attached thereto. The antibody can be a monoclonal antibody or a polyclonal antibody. The chemical reagent can be biotin a methyl chelate, such as N$_2$S$_2$ or N$_2$S$_4$, another chelator, such as EDTA, DPTA or TETA, or a dye, such as FITC. The chemical moiety is often a label, such as a radionuclide. The radionuclide can be Technicium or halogen radionuclide, such as $^{125}$I or $^{131}$I. In certain embodiments, the label is detectable by magnetic resonance imaging. The chemical moiety can be a biologically active molecule, such as a toxin, a drug and a chelate. Appropriate drugs include methotrexate, 5-fluoro-uracil, cis-platinum and adriamycin. An appropriate toxin is ricin A-chain.

Another aspect of the present invention is a pharmaceutical composition for immunoscintography. The composition includes labeled antibody conjugated with a chemical reagent at free amino groups disposed on the labeled antibody, so that the antibody has a reduced net positive charge compared to intact antibody, and a pharmaceutically excipient, carrier or base acceptable for immunoscintography.

Yet another aspect of the present invention is a method of preparing a labeled modified antibody having increased antigen binding specificity, decreased non-specific binding and decreased in vivo clearance time. The method includes the following steps: obtaining an intact antibody having binding specificity for an antigen to be detected, the native antibody having a plurality of free amino groups disposed thereon, reacting at least one of the free amino groups with a chemical agent to produce a modified antibody, such that the modified antibody has an isoelectric point lower than the isoelectric point of intact antibody, and labeling the modified antibody with a detectable label. The method produces a labeled modified antibody. The label in this method can be detectable by immunoscintography, such as by a gamma camera.

Still another aspect of the invention is a method of localizing an antigen in a mammal. This method includes obtaining a labeled modified antibody having binding specificity for the antigen to be localized. The labeled modified antibody has fewer free amino groups and a reduced isoelectric point compared to an unmodified antibody of the same type, and has incorporated therein a detectable label. The labeled modified antibody is administered to the mammal. The method allows the antigen and the labeled modified antibody to bind in vivo. The labeled modified antibody bound to the antigen is detected, thereby localizing the antigen. The antibody can be an intact antibody chemically modified at free amino groups. Such an intact antibody can be chemically conjugated with a heterobifunctional reagent or chemically conjugated with biotin.

A further aspect of the invention relates to a method of treating a disease state in a mammal. This method includes obtaining an intact antibody specific to the diseased tissues in the mammal. The intact antibody has disposed thereon a plurality of free amino groups. The method also includes modifying at least one of the free amino groups by conjugation with a chemical reagent other than a heterobifunctional reagent to produce a modified antibody. The modified antibody has a reduced isoelectric point compared to the intact antibody. A biologically active molecule is attached to a first attachment site disposed on the modified antibody other than the site of the chemical reagent. The antibody is then administered to the mammal, thereby treating the disease state.

DETAILED DESCRIPTION OF THE INVENTION have discovered that chemical modification of antibodies, including MAb's, human antibodies, genetically engineered antibodies, chimeric antibodies, synthesized antibodies and polyclonal antibodies, by conjugation with a reagent that modifies free amino groups can increase antigen binding specificity, decrease non-specific binding and decrease in vivo clearance times. Antibodies so modified have a reduced net positive charge compared to an intact antibody. Examples of reagents we have used to modify free amino groups in accordance with the present invention include a heterobifunctional reagent such as SPDP, or a biotinylating reagent. However, those of ordinary skill in the art will recognize that a wide variety of chemical reagents can be used to modify free amino groups and thereby lower the overall isoelectric point of the antibody. Thus, for example, methyl chelates, such as $N_2S_2$ and $N_2S_4$, other chelators, such as EDTA, DPTA and TETA, and a number of dyes, such as FITC, can all be used to achieve effective results in accordance with the present invention. In *Nucl. Med Biol.*, 18:179–185 (1991), a description of the binding of $N_2S_4$ to antibodies is described for a purpose other than described herein in accordance with the present invention. This article is hereby incorporated by reference.

Chemical modifications to free amino groups surprisingly led to enhanced accumulation of modified antibodies in target cells containing the antigen to which the antibodies will bind. Heterobifunctional reagents other than SPDP, including sulfosuccinimidyl 2-(p-azido salicylamido)ethyl-1,3'-dithiopropionate (SASD), sulfosuccinimidyl 2-(m-azido-o-nitrobenzamido)-ethyl-1,3'-dithiopropionate (SAND), sulfosuccinimidyl (4-azidophenyl-dithio)propionate (sulfo-SADP) and 2-aminothiolane•HCl (Traut's reagent), are believed to provide similar results when conjugated with antibodies in accordance with the present invention.

The modified antibodies of the present invention can be advantageously linked to another chemical moiety to provide a specific diagnostic or therapeutic benefit. For example, any of a variety of well known labels, such as a radionuclide or an enzyme, can be attached. A therapeutic moiety, such as an antineoplastic compound or toxin, can also be attached.

Both heterobifunctional agents and biotin have been previously used as linkers to attach labels and other moieties to antibodies. Biotin itself can function as a label in certain circumstances. However, neither biotin nor heterobifunctional agents have been used with the goal of modifying antibodies to achieve enhanced binding specificity, decreased non-specific binding and decreased in vivo clearance times. Thus, unlike in the present invention, previous antibodies have not had a modifying agent, such as a heterobifunctional agent or biotin, attached at a first site thereon and an attached label or other chemical moiety at a second site thereon. In the present invention, the second attachment site will generally not have an attached modifying agent of the same type as the modifying agent attached at the first attachment site.

It is thought that the enhanced accumulation of the modified antibodies is due to enhanced specific binding capacity. We have found that by conjugating, on average, only one PDP group per antibody molecule that a dramatic increase in the specificity of the molecule for its target cells occurs relative to unmodified antibody. Similar results were obtained using biotinylated antibodies.

We have also discovered that chemical modification of free amino groups on IgG by conjugation with a heterobifunctional reagent or biotin, advantageously, also enhanced clearance from normal tissues. Although not wishing to be bound by any particular explanation of this effect, it is conceivable that such modifications led to fragmentation of the antibody to a form having a molecular weight below the threshold for glomerular filtration, thus allowing for rapid elimination of the fragments. It is even possible that fragmentation of the antibody to the monovalent form of the antibody occurs. Whatever the exact form of the resulting fragments, the elimination of these fragments is, advantageously, not so rapid so as to curtail the diagnostic or therapeutic effectiveness of the modified antibodies.

As disclosed above, modified antibodies useful in the practice of the invention are chemically modified at free amino groups and are additionally labeled with a detectable label. Significantly, while either the antibody itself or the chemical reagent used to modify free amino groups can be labeled, we have also shown that labeling of the modified antibody at a site other than at free amino groups can provide an antibody useful in the practice of the invention. Further, when a label is chemically conjugated to the antibody, either before or after chemical modification of the antibody at free amino groups, that label can be attached to the antibody at a site other than at a free amino group and at a site other than the site of the amino group-modifying reagent when that reagent is a heterobifunctional reagent. As specifically disclosed herein, tyrosine residues present in the antibody protein can be modified by radioiodination. However, detectable labels that can be attached to antibody tyrosine residues are not limited to iodine. Other labels that can be attached to antibody tyrosine residues include halogen radionuclides, such as isotopes of F, Cl, Br, I and others. The attachment of such halogen radionuclides to antibodies is described in Wilbur, *Bioconj. Chem.*, 3:433–470 (1992), the disclosure of which is hereby incorporated by reference. Technicium radionuclides bind to other residues on the antiobody molecule. Further, other labels and methods of labeling antibody proteins are useful in the practice of the invention, as will be readily apparent to one having ordinary skill in the art. Those having ordinary skill in the art will appreciate that functional groups on amino acid side chains of an antibody protein can serve as label attachment sites. The choice of labels, attachment sites and methods of conjugating the label and the antibody will be appreciated by those having ordinary skill in the art. The important provision with respect to operability of the invention is that the modified antibody have a label attached.

Generally, we have discovered that antibodies chemically modified to have reduced isoelectric points (pIs) relative to unmodified antibodies exhibit improved target specificity. More specifically, our results demonstrated that chemical modification of free amino groups on antibodies can confer this improved targeting specificity. These chemical modifications may include modification by agents such as, but not limited to the above-referenced heterobifunctional agents and biotin. Indeed, any chemical modification of free amino groups present on an antibody that will effectively reduce the antibody pI will provide the improved targeting specificity.

While not wishing to be limited by any particular theory to explain the origin of this improvement, we postulate that non-specific antibody binding is due partly to nonspecific electrostatic interactions. This is reasonable in light of the observation that MAb's are positively charged at physiological pH while mammalian cells are negatively charged (Eichmann et al. *J Exp. Med*. 131:207 (1970); Silva Filho et al. *J Leukocyte Biol*. 41:143 (1987)). Thus, alteration of the positive charge character of intact antibody effectively diminishes non-specific binding due to interactions between negatively charged tissues and positively charged antibody proteins. By minimizing these non-specific interactions, antibody specificity attributable to the antigen-binding domains of the antibody is predominantly responsible for determining binding specificity. Thus, any antibody having a plurality of aminoside moieties modified such that the pI of the of the antibody is reduced relative to the unmodified antibody will exhibit improved target specificity by virtue of having reduced non-specific interactions with non-cognate antigens. However, we also discovered that a second feature of antibodies modified in accordance with the invention renders them particularly useful for in vivo antigen localization.

Two factors that can improve the signal-to-noise ratio, which can be represented as the "tumor/organ ratio," in antibody-based antigen imaging procedures are: (1) increased tumor localization, and (2) decreased levels of non-specifically bound labeled antibody. We have now discovered that MAb's chemically modified to have isoelectric points reduced relative to the unmodified intact MAb can advantageously increase binding specificity while reducing non-specific binding and decreasing the whole-body clearance time relative to unmodified antibody.

We have further discovered that increased antibody specificity and localization capabilities can be achieved using chemically modified antibodies having disposed thereon a detectable label. Such a label can, for example, be a radionuclide. More specifically, we have now discovered that antibodies modified to contain biotin moieties exhibit substantially improved capacity for binding antigen. As disclosed below, labeled biotinylated antibodies have been used in a method for localizing tumor cells in vivo. In the practice of the invented method, it is essential for the chemically modified antibody te be labeled directly. This contrasts with methods employing antibodies labeled indirectly as described by Khawli et al. in *Antibody, Immunoconjugates, and Radiopharmaceuticals*, 6:13 (1993), the disclosure of which is hereby incorporated by reference.

Thus, reagents useful in procedures for improved tumor localization can be produced by obtaining an antibody having binding specificity for a desired target antigen, chemically modifying free amino groups on the antibody using a reagent such as a heterobifunctional reagent or biotin and then labeling the antibody with a detectable label such as a radionuclide. In practice, the order of the chemical modifying and radiolabeling steps is optional. Further, a step for radiolabeling substantially purified antibodies can be eliminated if the antibodies employed in the procedure are MAb's and if the hybridoma producing those MAb's is propagated in growth medium containing labeled precursors that are incorporated into the MAb products of the hybridoma. Thus, for example, radiolabeled and biotinylated MAb's useful in connection with the invention can be produced by propagating the MAb-producing cell line in growth medium containing radiolabeled amino acids, collecting the radiolabeled MAb's, and biotinylating the radiolabeled MAb's. Alternative methods for labeling antibodies, either before or after a biotinylation step, will be apparent to those having ordinary skill in the art.

The method described herein, while related to that disclosed by Khawli et al., in *Antibody, Immunoconjugates, and Radiopharmaceuticals*, supra, advantageously involves fewer steps for imaging tumor cell antigens in vivo, and unexpectedly provides better results than simply using radiolabeled antibodies lacking biotin groups. Thus, herein we disclose that biotinylated antibodies exhibit improved targeting when compared with nonbiotinylated antibodies. Since an antibody useful in connection with the invention can be detected by virtue of a label carried on the antibody, the presence of biotin groups on the labeled antibody provides obvious advantages with respect to targeting and detection. Thus, essential features of antibodies useful in connection with the invention and that the antibodies: (1) have aminoside moieties chemically modified such that the pI of the modified antibody is reduced relative to the unmodified antibody, and (2) harbor a label that can be detected by a detection means.

The modified antibodies of the present invention, advantageously, have surprisingly enhanced diagnostic and therapeutic effectiveness relative to fragments of antibodies, such as F(ab') or F(ab')$_2$.

The following example shows an exemplary method for the introduction of, on average, one PDP group to a monoclonal antibody.

EXAMPLE 1

Modification of Lym-1 with SPDP Lym-1 (IgG$_{2a}$), the monoclonal antibody against B cell lymphoma was obtained as in Epstein, A. L. et al., Two New Monoclonal antibodies, Lym-1 and Lym-2, Reactive with Human B-lymphocytes and Derived Tumors, with Immunodiagnostic and Immunoreactive Potential, *Cancer Res*. 47: 830–840 (1987), the disclosure of which is hereby incorporated by reference. The Lym-1 MAb's were functionalized using SPDP, a heterobifunctional reagent which reacts with free amino groups on antibodies as in Carlson, J. et al., Protein Thiolation and Reversible Protein-Protein Conjugation: N-succinimidyl 3-(2-pyridyldithio)propionate, A New Heterobifunctional Reagent, *Biochem. J*. 173: 723–737 (1978), the disclosure of which is hereby incorporated by reference. To a 5 mL test tube containing 1 mL of Lym-1 (10 mg/mL) in PBS, pH 7.2, was added 20 µL of 3 mg SPDP in 1 mL ethanol and 40 µL, N,N-dimethylformamide. This mixture was incubated for 15 minutes at room temperature with continuous mixing using an orbital shaker apparatus set at normal speed. After incubation, the functionalized Lym-1 solution was purified by passage through a PD-10 column equilibrated with PBS.

The degree of functionalization of Lym-1 with SPDP was determined to be an average of one PDP group per molecule by measurement of release of pyridine-2-thione at 343 nm after reduction of an aliquot of the Lym-1 solution with molar excess of 7 mg dithioerythritol in phosphate buffer saline solution (PBS), pH 7.2., as in Grassetti, D. R. and Murray, J. F., Determination of Sulfhydryl Groups with 2,2'- or 4,4'-dithiodipyridine, *Arch. Biochem. Biophys.* 119: 41–49 (1967), the disclosure of which is hereby incorporated by reference.

The modified antibody from Example 1 was analyzed by Fast Protein Liquid Chromatography (FPLC) in order to show that the antibodies remained substantially intact. This analysis is shown in Example 2.

EXAMPLE 2

Analysis of Modified Lym-1 through Fast protein Liquid Chromatography (FPLC)

Analysis of modified antibody, from Example 1, was achieved by Fast protein Liquid Chromatography (FPLC) equipped with a fixed wavelength UV spectrophotometer set at 280 nm. Size exclusion chromatography was performed on a superose-12 column (Pharmacia) with PBS pH 7.2 as the solvent system, eluting at flow rate of 1 mL/min. The modified Lym-1 appeared at a retention time of 690 seconds, identical to the retention time of unlabeled intact Lym-1.

Thus, Example 2 shows that the SPDP-modified antibodies behaved virtually identically to the unmodified antibodies in FPLC. This data shows that the modification likely did not lead to breakdown of the intact molecules in vitro.

In order to further study the modified MAb's for in vivo testing, radiolabelling of the modified MAb's was performed. The radiolabelling is shown in Example 3.

EXAMPLE 3

Direct Radioiodination of Modified Lym-1

One batch of PDP modified Lym-1 and intact Lym-1 were iodinated with $^{125}$I, and another batch labeled with $^{131}$I using the modified chloramine T method of Mills, S. L. et al., $^{125}$I Radiolabelling of Monoclonal antibodies for In Vivo Procedures, *Hybridoma* 5: 265–275 (1986), the disclosure of which is hereby incorporated by reference. Briefly, to a 5 mL test tube containing 100 μg monoclonal antibody in 100 μL PBS, was added the appropriate iodine isotope, $^{125}$I or $^{131}$I depending on the batch, and 10 μL of 43 mM aqueous solution of chloramine T. The reaction was quenched after 3 minutes with 20 μL of 120 mM solution of sodium metabisulfite. The radiolabeled antibodies were purified using a Sephadex G-25 column. This column consisted of a serological plastic pipette (8 mm×200 mm) plugged at the end with cotton ($V_o$=4.5 mL, $V_t$=12 mL). Each reaction mixture was loaded on a column and eluted with PBS, pH 7.2. Individual tubes containing 1 mL aliquots were counted, and the radiolabeled antibodies were recovered in tube 6 in 85–90% yield. These radiolabeled antibodies were stored in the refrigerator and administered to mice within 4 hours of labeling.

The radiolabeled MAb's from Example 3 were subjected to Instant Thin Layer Chromatography (ITLC) in order to determine the purity of the labeled MAb's. This analysis is shown in Example 4.

EXAMPLE 4

Analysis of Radiolabeled Modified Lym-1 through Instant Thin Layer Chromatography (ITLC)

Modified Lym-1 radiolabeled with $^{131}$I and modified Lym-1 radiolabeled with $^{125}$I via the chloramine T method of Example 3 were analyzed using an analytical ITLC system consisting of silica gel impregnated glass fiber. Strips (2×20 cm) were activated by heating at 110–½° C. for 15 minutes prior to use; spotted with 1 μL of sample; air-dried and eluted with MeOH/H$_2$O (80:20) for approximately 12 cm; again air-dried, cut in half and counted to determine protein-bound and non-protein-bound radioactivity. Both forms of radiolabeled Lym-1 antibodies had an $R_f$ value of 0 and showed radiochemical purity of ≧99%. Analysis of intact Lym-1 labeled in the same way as in Example 3 revealed the same purity.

Thus, Example 4 shows that high purity radiolabeled antibodies could be obtained. The immunoreactivities of these radiolabeled MAb's were tested by their ability to bind to Raji cells. This analysis is shown in Example 5.

EXAMPLE 5

Analysis of Radiolabeled Modified Lym-1 through Immunoreactivity Assessment

The in vitro immunoreactivities of the radiolabeled modified Lym-1 and intact Lym-1 were evaluated by conventional live assay of 10$^6$ Raji cells/tube by the method of Epstein, A. L. et al., supra. Briefly, Raji cells resuspended in 100 μL of 1% bovine serum albumin in PBS was pipetted into a triplicate set of test tubes. One hundred μL of the labeled Lym-1 was added to each test tube (100,100 cpm/tube) and incubated for 30 minutes at room temperature with continuous mixing using an orbital shaker. After incubation, the cells were washed three times with 1% bovine serum in PBS by spinning the tubes at 1000 rpm for 5 minutes, decanting the supernatant and resuspending the cells in 200 μL PBS. Following completion of the washes, bound Lym-1 was detected by measuring the radioactivity bound to the cells using a gamma counter. The results showed that the binding activity of the modified Lym-1 was 87%, whereas the intact Lym-1, which served as a standard control, had a binding activity of 80%.

Thus, Example 5 shows that the modified Lym-1 was more immunoreactive in vitro than the unmodified Lym-1. In order to gain a preliminary assessment of the stability of the activity of the modified antibodies in vivo, modified MAb's were analyzed for their stability in serum, as shown in Example 6.

EXAMPLE 6

Analysis of Radiolabeled Modified Lym-1 through Serum Stability

Monoclonal antibodies of modified Lym-1 and intact Lym-1 which was labeled directly with I-125 were added to each of several triplicate sets of fresh mouse serum to a final concentration of 100 μg/mL. The tubes were incubated at 37–½° C. in a humidified incubator maintained in 5% CO$_2$ in air. At times between 0 and 8 days, protein-bound activity was determined by adding 900 μL of 100% trichloroacetic acid (TCA) to 100 μL aliquots. After a five-minute incubation at room temperature, protein precipitates were sedimented by centrifugation, and 500 μL of supernatant were withdrawn from each tube and counted for radioactivity in a gamma counter. Data were expressed as the mean percentage counts precipitated minus that of the control tubes. The results showed that at each time point after incubation, modified $^{125}$I-Lym-1 was as stable as the $^{125}$I labeled intact Lym-1 which served as a standard control. The results further showed that ≧92% of activity present in the modified Lym-1 following an 8-day incubation at 37–½° C. was TCA precipitable.

Thus, Example 6 showed that the stability of the activity of the modified antibodies was maintained in serum for at least 8 days. In order to evaluate whether the modified MAb's remained intact after incubation in serum, HPLC analysis of the modified Lym-1 after incubation was performed, as shown in Example 7.

EXAMPLE 7

Analysis of Modified Lym-1 by HPLC

HPLC analyses were performed on a Waters system equipped with size exclusion columns (SW 300) with 0.1M neutral phosphate buffer as eluting solvent and a flow rate of 1 mL/min. The eluate was detected with a radioisotope detector. The labeled modified Lym-1 product mixture from Example 6 revealed one major peak of a low molecular weight species with an elution time of 750 seconds, plus a small quantity at 690 seconds. The intact Lym-1 gave a single peak with a retention time of 690 seconds.

Thus, Example 7 shows that the serum incubated modified Lym-1 samples had an apparent molecular weight in HPLC analysis lower than that of intact Lym-1. In contrast, Example 2 showed that unincubated modified Lym-1 had an identical retention time to intact Lym-1. Thus, the modified Lym-1 showed an apparent loss of molecular weight in FPLC analysis upon incubation in serum.

To further verify the apparent loss of molecular weight of the modified Lym-1 upon incubation in serum, polyacrylamide gel electrophoresis of the samples was performed, as shown in Example 8.

EXAMPLE 8

Analysis of Radiolabeled Modified Lym-1 through SDS-Polyacrylamide Gel Electrophoresis (SDS-PAGE)

The same aliquots of each incubated serum mixture from Example 6 were serially checked by non-reduced SDS-PAGE. For this study, samples were run on 10% acrylamide gels, dried carefully and exposed in the usual way to a photographic film as in Laemmli, U. K., Cleavage of Structural Proteins During the Assembly of the Head of Bacteriophage T4, *Nature* 227: 680–685 (1970), the disclosure of which is hereby incorporated by reference. This analysis revealed that intact $^{125}$I-Lym-1 was evident at $M_r$ 200,000, whereas modified $^{125}$I-Lym-1 was observed at a distinct band corresponding to a smaller molecular weight at approximately $M_r$ 116,000. Thus, the present example shows that incubation of the modified antibodies in serum results in modified apparent molecular weight on acrylamide gels, verifying the results of HPLC analysis.

EXAMPLE 9

Test for Deiodination of Labeled Lym-1 in Serum

The same samples from Example 6 were also examined over an 8-day study to see if there had been any loss of radioactivity from the radiolabeled Lym-1; such loss can be interpreted as evidence of deiodination in serum. The data showed virtually no loss of radioactivity over this period, confirming that a very stable attachment of iodine had been obtained in these immunoconjugates.

Thus, Examples 7–9 show that the modified antibodies while retaining virtually full activity after incubation in serum, appeared to break down into molecules of apparent molecular weight of 116,000. As stated above, it is possible that this loss of molecular weight is due to the breakdown of the antibodies into their monovalent form. In any event, it is believed that the loss in apparent molecular weight is due to the breakdown of the modified antibodies into fragments thereof.

After discovering the foregoing unexpected change in apparent molecular weight of the modified antibodies when incubated in serum, we tested the stability of the modified MAb's in vivo. We performed these in vivo tests in order to determine total body clearance time. An example of these tests is shown in Example 10.

EXAMPLE 10

Total Body Clearance

Experiments were performed in which three groups of athymic nude mice (n=5) were given intraperitoneal injections of (a) intact antibody, (b) F(ab')$_2$ fragments, or (c) modified antibody of Lym-1 labeled with I-131 using the chloramine T method. The whole-body activity at injection and serially thereafter was measured with a dosimeter. This study demonstrated that the total body clearance of radioactivity varied with the antibody preparation. Results are shown in FIG. 2.

Figure 2:
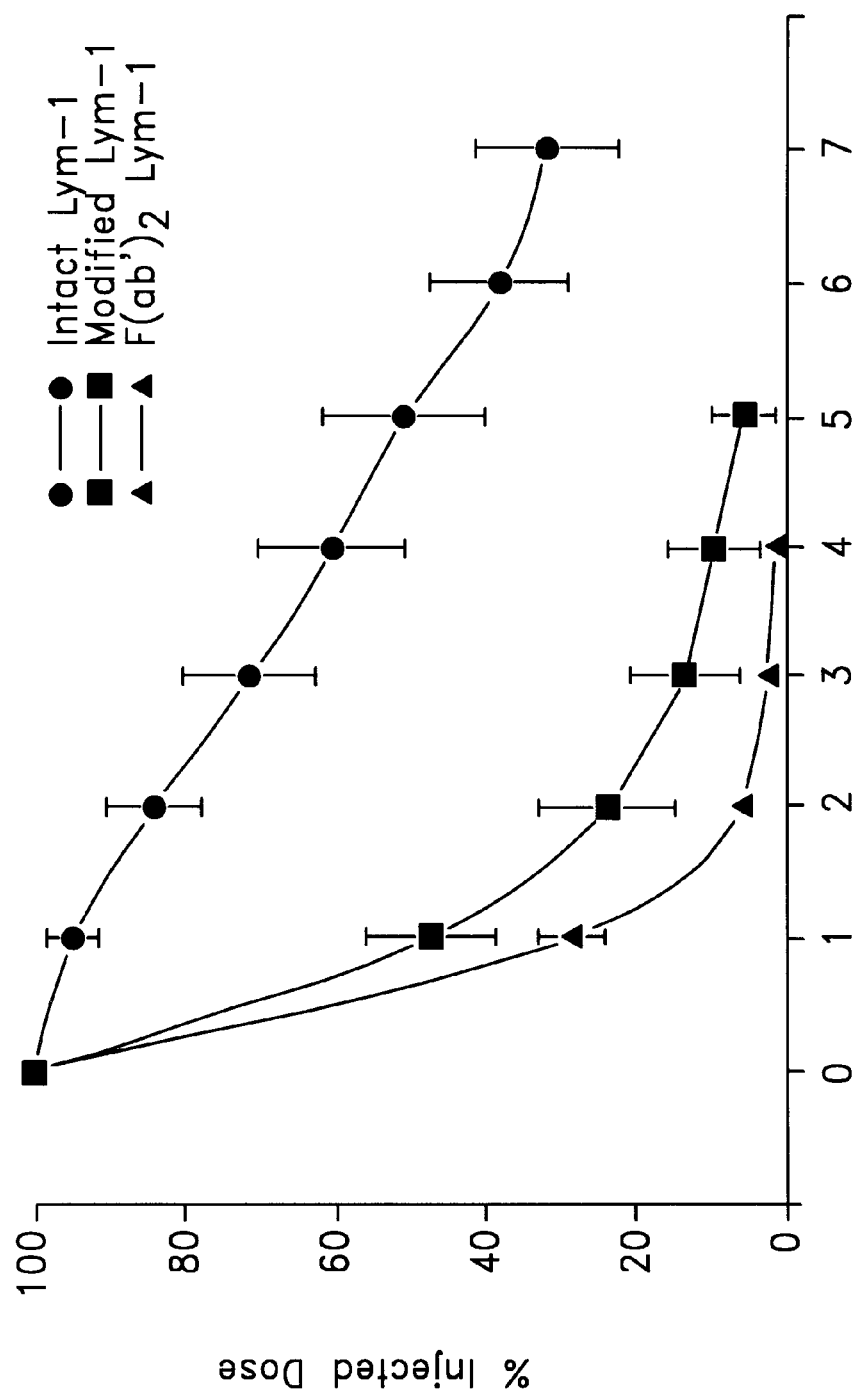
FIG. 2 shows whole body retention of different preparations of radio-labeled MAb's Lym-1 in athymic nude mice.

FIG. 2 shows that the modified Lym-1 cleared from the whole body faster, with a biological half-life ($t_{1/2}$) of 20 hours, than the intact Lym-1 ($t_{1/2}$=5 days). The clearance of F(ab')$_2$ fragments was, however, two times faster, with a biological half-life of 10 hours, than the modified Lym-1. The data showed that modified Lym-1 is cleared at a rate intermediate between the rapidly-cleared F(ab')$_2$ fragments and the slowly-cleared intact antibody.

Thus, it can be seen from the data from Example 10 that the modified antibodies are cleared from the body more rapidly than the relatively highly persistent intact antibodies, yet not so rapidly as F(ab')$_2$ fragments.

An ideal agent for immunotherapy would persist in the bloodstream for a period sufficiently long as to produce the desired toxic effect, yet not so long as to cause unintended toxic side effects. The data from Example 10 suggested that the modified antibodies exhibited potentially ideal persistence times when used in immunotherapy.

As discussed above, an agent for immunotherapy would also be highly specific towards its target cells. Thus, we tested the specificity of the modified MAb's relative to both intact MAb's and the F(ab')$_2$ fragments in the following examples. Example 11 shows the methods used in all of the subsequent biodistribution studies.

EXAMPLE 11

Biodistribution Studies

Two groups of six-week-old nude mice were injected with Raji cells (10$^7$) subcutaneously in the thigh region. The tumors were grown for three weeks until they became larger than 1 cm in diameter. Paired-label studies, as described below, were performed using each group of mice. In the first group (n=6), each mouse was injected i.p. with a 0.2 mL inoculum containing 10 µg of modified Lym-1 labeled with I-131 at 12 µCi/µg (120 µCi/mouse), and 10 µg of intact Lym-1 labeled with I-125 at 2.5µCi/µg (25 µCi/mouse). In the second group (n=4), mice received a 0.2 mL inoculum containing 10 µg of modified Lym-1 labeled with I-131 at 12 µCi/µg (120 µCi/mouse), and 10 µg of F(ab')$_2$ fragments labeled with I-125 at 2.5 µCi/tig (25 µCi/mouse). In all experiments, mice were sacrificed by cervical dislocation at preselected times, post-injection, and various organs, blood and tumor were removed and weighed on an analytical balance. The samples were then counted in a gamma counter to determine the $^{131}$I and $^{125}$I activity. $^{125}$I counts were adjusted for cross-over from the $^{131}$I channel by subtracting 17% of $^{133}$I channel counts, a formula that was determined experimentally using a 1282 Compugamma gamma counter (LKB). The data were also corrected for the radiation decay of the $^{131}$I isotope according to the days on which the animals were sacrificed. For each mouse, data was expressed as cpm per gram tumor/cpm per gram organ, % dose/gram, and % dose/organ From these data, the mean and standard deviation were calculated for each group.

Example 12 compares the biodistribution of the modified MAb's to intact MAb's using the methods of Example 11.

EXAMPLE 12

Biodistribution Study of Modified Lym-1 vs. Intact Lym-1

For this study, the intact Lym-1 antibody was compared to the modified Lym-1 antibody in the methods of Example 11. Intact Lym-1 produced a blood activity of 0.64% ID/g at 7 days after injection, as reported in Table I. At the end of the same time interval, the tumor had an activity of 3.92% ID/g.

As reported in Table I, compared to the intact Lym-1, the modified Lym-1 cleared from blood faster and produced a blood activity of 0.14% ID/g at 7 days. At the end of the same time interval, the tumor produced 7.7%, which tended to be significantly higher than the corresponding activities of the intact Lym-1.

Figure 3:
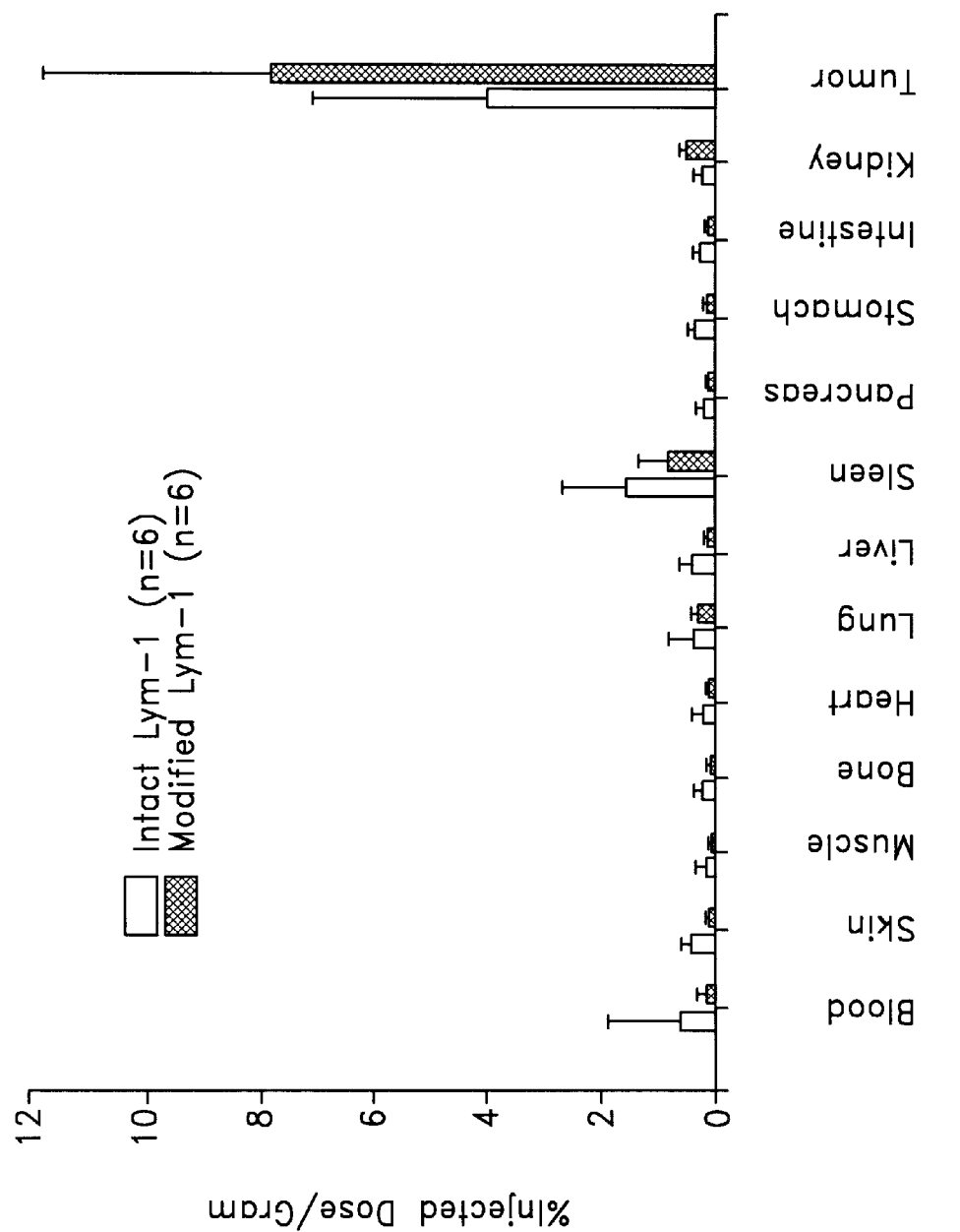
FIG. 3 shows the biodistribution as % of injected dose/gram of MAb's Lym-1 and modified Lym-1 in human lymphoma-bearing nude mice seven days after injection.
Figure 4:
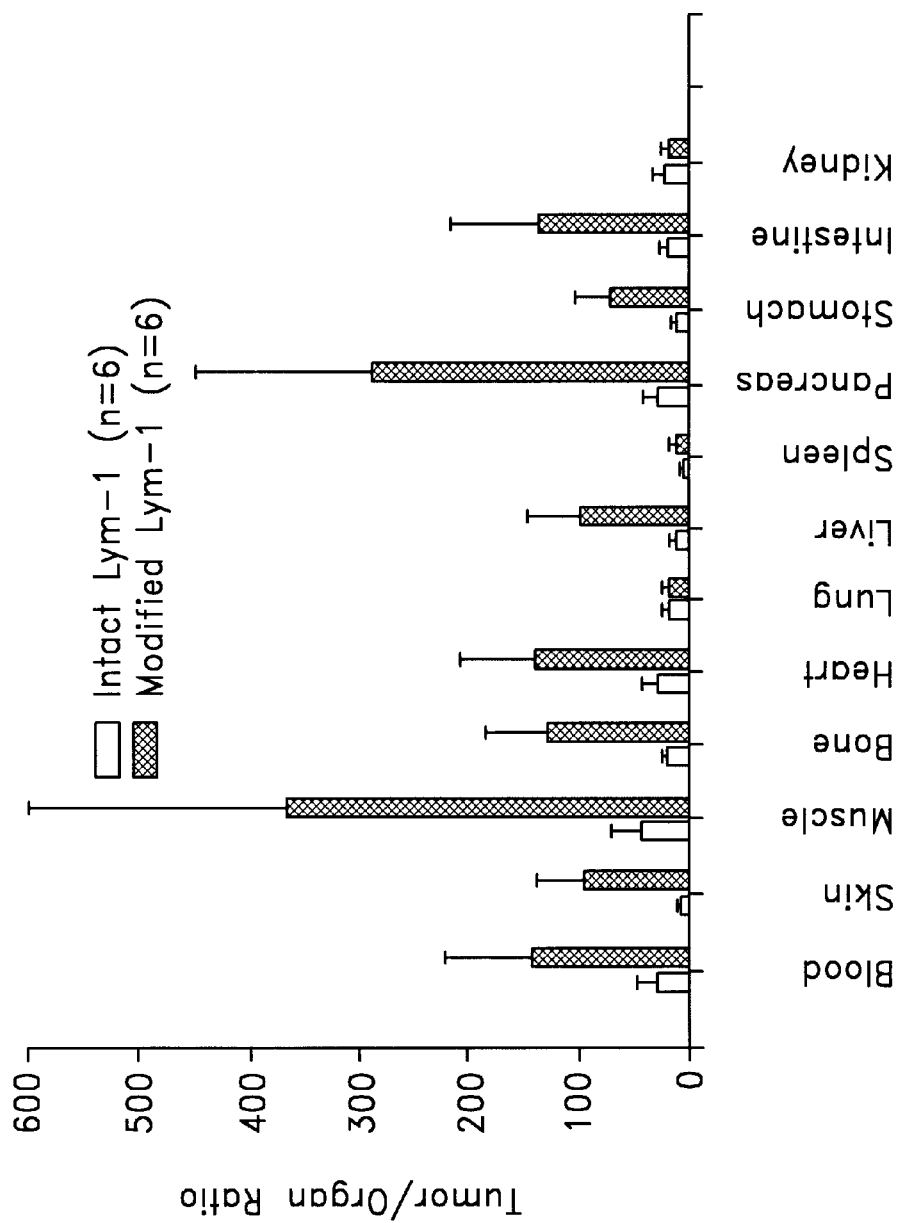
FIG. 4 shows the biodistribution as tumor/organ ratios of MAb's Lym-1 and Modified Lym-1 in human lymphoma-bearing nude mice seven days after injection.

Results of antibody reactivity from Example 12 in several organs are reported in Table I and shown graphically in FIG. 3 (% dose/gram) and FIG. 4 (tumor/organ).

TABLE I

BIODISTRIBUTION OF MODIFIED AND INTACT MONOCLONAL ANTIBODY LYM-1 IN RAJI TUMOR-BEARING NUDE MICE (N = 6) 7 DAYS AFTER INJECTION

| Organ | cpm/g tumor cpm/g organ | % dose/g | % dose/organ |
|---|---|---|---|
| Modified Lym-1 | | | |
| Blood | 140.07(81.30)* | 0.14(0.20) | — |
| Skin | 93.98(43.40) | 0.09(0.04) | — |
| Muscle | 364.53(232.97) | 0.03(0.03) | — |
| Bone | 126.96(55.86) | 0.06(0.02) | — |
| Heart | 137.34(67.96) | 0.07(0.04) | 0.01(0.00) |
| Lung | 28.31(10.34) | 0.28(0.10) | 0.06(0.02) |
| Liver | 96.80(49.03) | 0.09(0.05) | 0.15(0.08) |
| Spleen | 12.02(5.62) | 0.79(0.53) | 0.03(0.01) |
| Pancreas | 286.43(159.92) | 0.04(0.02) | 0.00(0.00) |
| Stomach | 71.21(30.72) | 0.11(0.03) | 0.02(0.01) |
| Intestine | 133.31(80.82) | 0.07(0.04) | — |
| Kidney | 17.63(7.63) | 0.45(0.12) | 0.14(0.03) |
| Tumor | — | 7.70(3.95) | 2.98(1.71) |

TABLE I-continued

BIODISTRIBUTION OF MODIFIED AND INTACT MONOCLONAL ANTIBODY LYM-1 IN RAJI TUMOR-BEARING NUDE MICE (N = 6) 7 DAYS AFTER INJECTION

| Organ | cpm/g tumor cpm/g organ | % dose/g | % dose/organ |
|---|---|---|---|
| Intact Lym-1 (Control) | | | |
| Blood | 30.72(17.74) | 0.64(1.26) | — |
| Skin | 8.83(3.05) | 0.41(0.20) | — |
| Muscle | 44.39(26.16) | 0.15(0.21) | — |
| Bone | 19.49(6.08) | 0.21(0.18) | — |
| Heart | 28.79(13.76) | 0.19(0.22) | 0.02(0.02) |
| Lung | 16.98(8.22) | 0.36(0.46) | 0.07(0.01) |
| Liver | 11.84(5.95) | 0.37(0.25) | 0.59(0.46) |
| Spleen | 3.93(3.74) | 1.52(1.14) | 0.06(0.03) |
| Pancreas | 29.35(12.88) | 0.16(0.17) | 0.02(0.02) |
| Stomach | 11.00(4.55) | 0.32(0.11) | 0.07(0.03) |
| Intestine | 18.06(8.79) | 0.23(0.13) | — |
| Kidney | 22.44(10.61) | 0.20(0.17) | 0.06(0.05) |
| Tumor | — | 3.92(3.11) | 1.02(0.27) |

*Mean (standard deviation).

It can be seen from FIG. 3 that the modified antibodies produced a higher signal in the tumor than the intact antibodies. Additionally, the modified antibodies reacted less strongly than the intact MAb's for every organ tested, except for the kidney. It is not unexpected that a higher signal would be found in the kidney, because the antibodies are expected to be cleared through this organ. Due to the more rapid clearance rate of the modified MAb's relative to intact MAb's found in Example 10, a higher amount of modified MAb's in the kidney would be expected.

Referring to FIG. 4, showing the same data as FIG. 3 in a different form, it can be seen that the modified MAb's produced a significantly higher tumor/organ ratio than intact MAb's in every organ tested, except for kidney. Thus, it would be expected that the modified antibodies would produce a significantly lower background when used in immunoscintography. Moreover, it would also be expected that the modified antibodies would be more effective when used in immunotherapies due both to its higher affinity for tumor and lower affinity for non-target tissues. When used in immunotherapies, the modified antibodies would, thus, be expected to be more highly toxic to tumors and less toxic to non-target tissues. The immunotherapeutic use of the modified antibodies of the present invention is hereinafter explained in further detail.

We next compared the biodistribution of the modified MAb's with F(ab')$_2$ fragments of the otherwise unmodified antibody. Example 13 is illustrative of these experiments.

EXAMPLE 13

Biodistribution Study of Modified Lym-1 vs. F(ab'), Fragments of Lym-1

For this study, the F(ab')$_2$ fragments were compared with the modified Lym-1 MAb's. Experiments were performed as in Example 11. Results are reported in Table II and shown graphically in FIGS. 4 and 5.

TABLE II

BIODISTRIBUTION OF MODIFIED AND INTACT MONOCLONAL ANTIBODY LYM-1 IN RAJI TUMOR-BEARING NUDE MICE (N = 4) 5 DAYS AFTER INJECTION

| Organ | cpm/g tumor cpm/g organ | % dose/g | % dose/organ |
|---|---|---|---|
| Modified Lym-1 | | | |
| Blood | 39.59(14.84)* | 0.09(0.03) | — |
| Skin | 13.69(3.15) | 0.24(0.06) | — |
| Muscle | 75.32(16.22) | 0.04(0.01) | — |
| Bone | 26.79(7.18) | 0.12(0.04) | — |
| Heart | 44.42(11.34) | 0.08(0.04) | 0.01(0.01) |
| Lung | 15.78(3.88) | 0.21(0.07) | 0.04(0.01) |
| Liver | 12.19(4.25) | 0.29(0.12) | 0.27(0.10) |
| Spleen | 2.68(1.01) | 1.34(0.55) | 0.07(0.03) |
| Pancreas | 42.17(11.23) | 0.08(0.03) | 0.01(0.00) |
| Stomach | 14.16(4.43) | 0.24(0.07) | 0.05(0.02) |
| Intestine | 28.36(9.96) | 0.12(0.05) | — |
| Kidney | 12.53(3.15) | 0.27(0.09) | 0.09(0.03) |
| Tumor | — | 3.18(0.89) | 3.16(1.09) |
| F(ab')$_2$ Fragments (Control) | | | |
| Blood | 29.27(13.17) | 0.05(0.02) | — |
| Skin | 10.54(2.78) | 0.12(0.02) | — |
| Muscle | 55.50(14.49) | 0.02(0.01) | — |
| Bone | 23.73(7.89) | 0.06(0.02) | — |
| Heart | 35.19(11.01) | 0.04(0.02) | 0.00(0.00) |
| Lung | 12.57(3.69) | 0.10(0.03) | 0.02(0.00) |
| Liver | 10.43(4.20) | 0.13(0.05) | 0.12(0.04) |
| Spleen | 2.59(1.03) | 0.54(0.21) | 0.03(0.01) |
| Pancreas | 31.55(9.82) | 0.04(0.02) | 0.00(0.00) |
| Stomach | 8.03(3.31) | 0.17(0.06) | 0.03(0.01) |
| Intestine | 22.27(7.93) | 0.06(0.02) | — |
| Kidney | 10.05(2.71) | 0.13(0.04) | 0.04(0.01) |
| Tumor | — | 1.23(0.24) | 1.42(0.48) |

*Mean (standard deviation).

Figure 5:
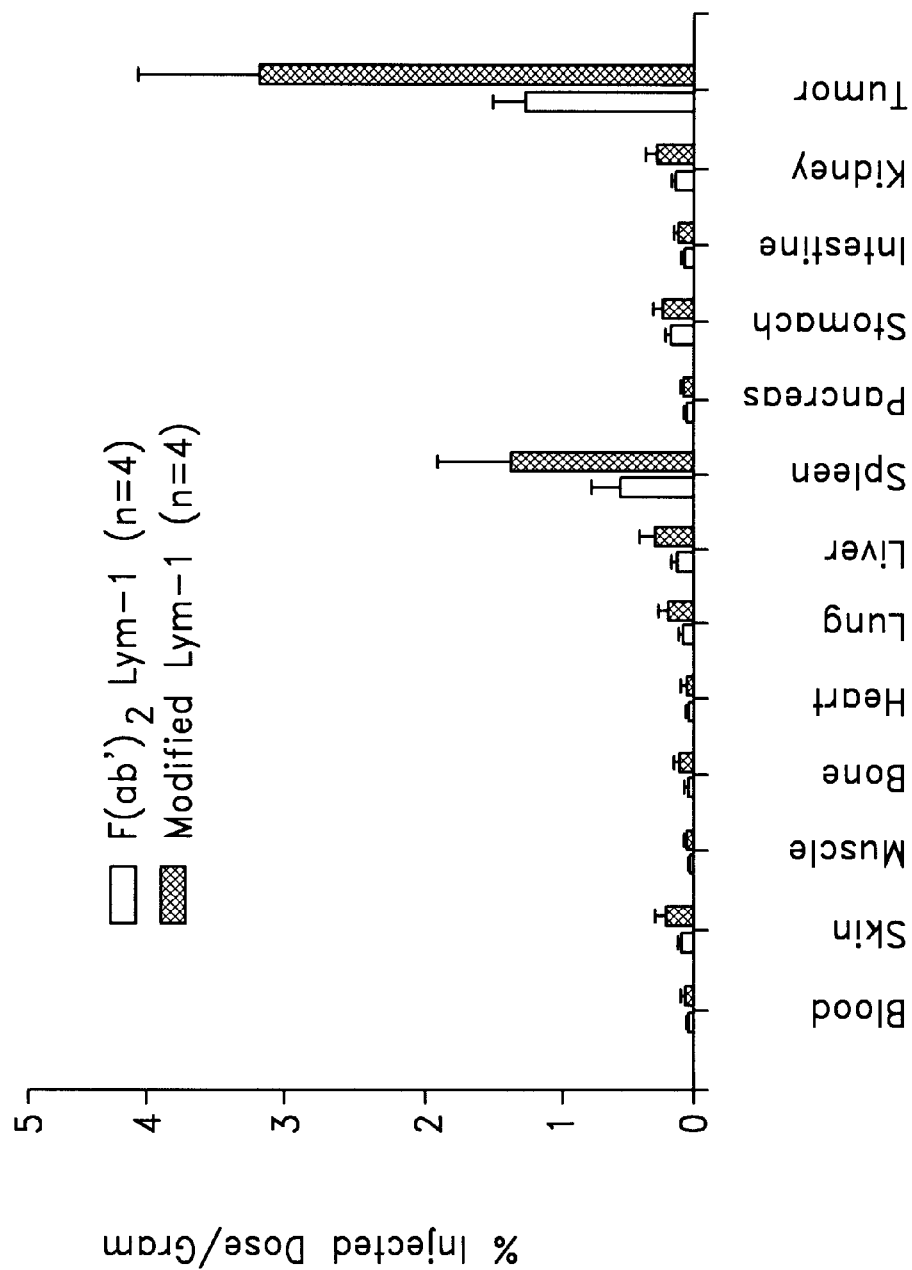
FIG. 5 shows the biodistribution as % of injected dose/gram of MAb's Lym-1 F(ab')$_2$ and Modified Lym-1 in human lymphoma-bearing nude mice five days after injection.

Table II shows that the modified Lym-1 cleared more slowly from the blood than the F(ab')$_2$ fragments. The modified Lym-1 produced a blood activity of 0.09% ID/g higher than the fragments (0.05%) at 5 days post-injection. FIG. 5 shows that the tumor activity of the modified Lym-1 was about two-and-one-half times higher than the corresponding activity of the F(ab')$_2$ fragments. The activity of the modified Lym-1 was higher than the F(ab')$_2$ fragments for all of the various organs tested, including kidney. This is consistent with the theory that more rapidly cleared antibodies accumulate in the kidney.

Figure 6:
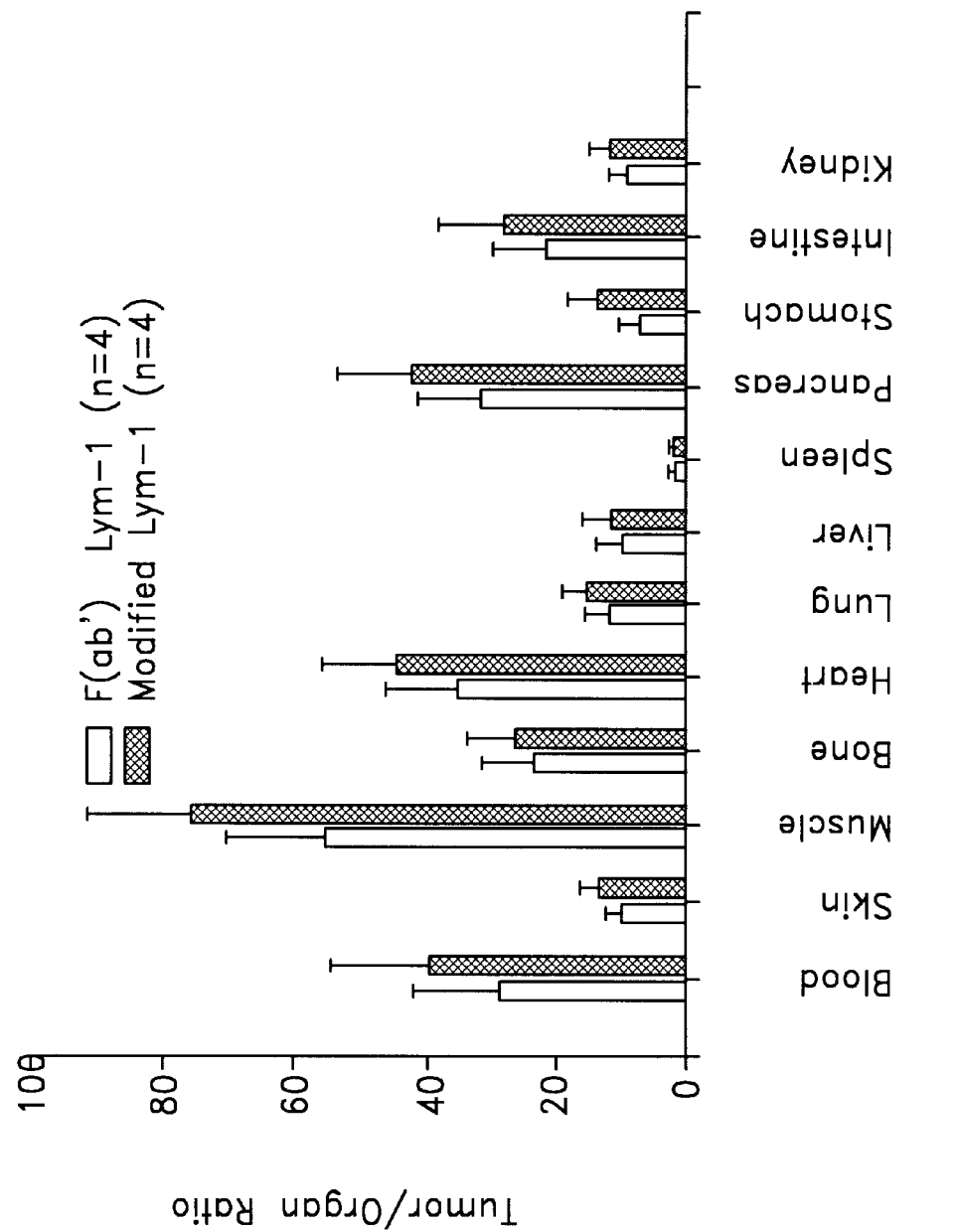
FIG. 6 shows the biodistribution as tumor/organ ratio of MAb's Lym-1 F(ab')$_2$ and Modified Lym-1 in human lymphoma-bearing nude mice five days after injection.

Moreover, FIG. 6 shows that the tumor-to-organ ratios for modified Lym-1 are higher than those of the F(ab')$_2$ fragments for all of the organs tested. Thus, the experiments of Examples 12 and 13 confirm that the modified antibodies of the present invention have a higher activity for their target tumor than either intact MAb's or F(ab')$_2$ fragments. Additionally, the tumor-to-organ data of these experiments shows that the modified antibodies have higher specificity for tumor than either the intact MAb's or F(ab')$_2$ fragments.

Thus, we tested the ability of the modified MAb's of the present invention to produce improved immunoscintographic results. One example of these tests is shown in Example 14.

EXAMPLE 14

Imaging Studies of Lym-1

Figure 7:
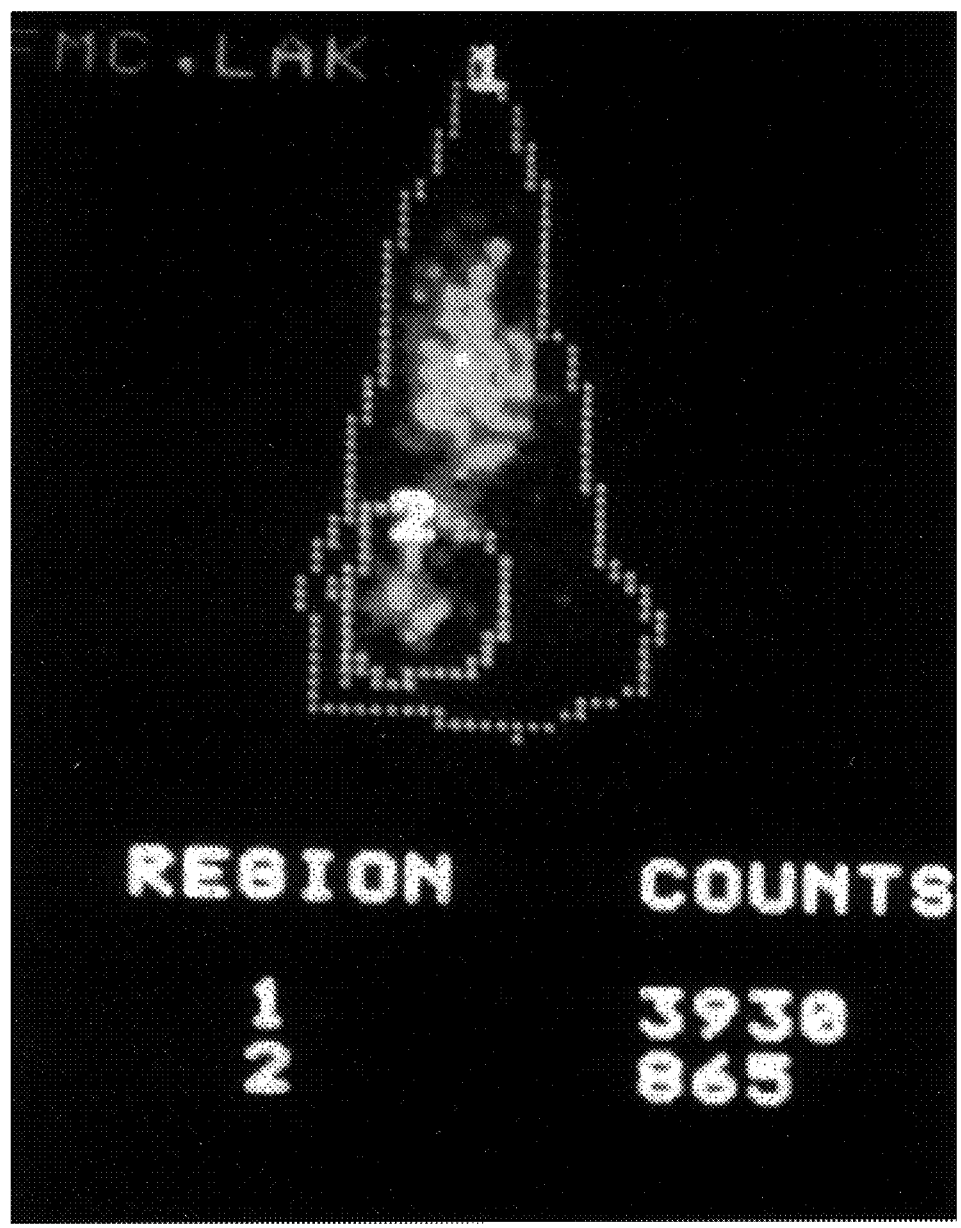
FIG. 7 shows the image obtained on day 7 after injection of I-131 labeled intact Lym-1.
Figure 8:
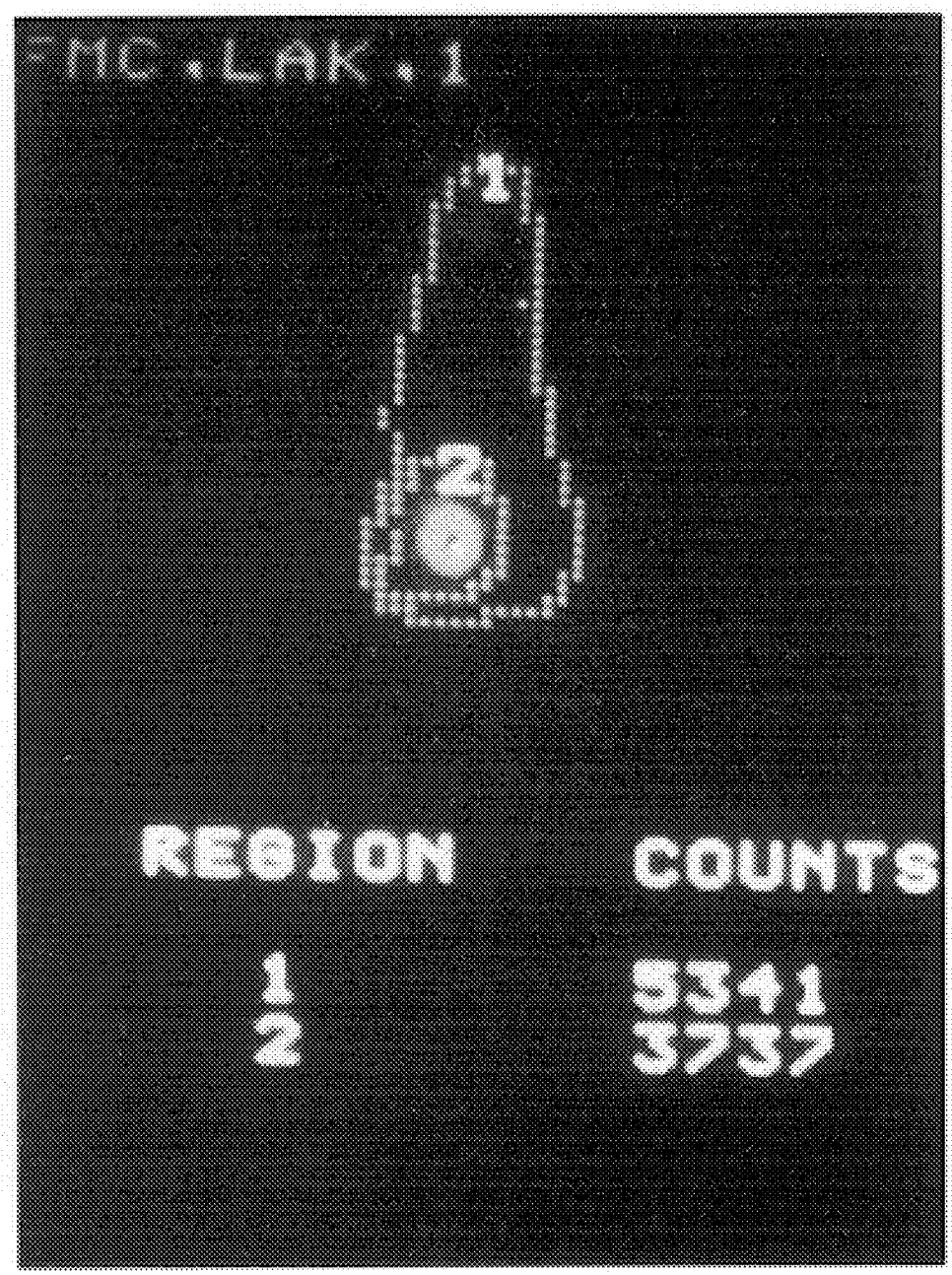
FIG. 8 shows the image obtained on day 7 after injection of I-131 labeled modified Lym-1.

Tumor-bearing nude mice were imaged using a pinhole collimator and a spectrum 91 gamma camera (Raytheon). Image analyses of these animals provided an estimate of tumor/whole body antibody distribution after injection. Seven days after injection, the mice were anesthetized with 2 mg Ketamine HCl and 0.4 mg Xylazine administered as a 0.2 mL s.c. inoculation. The immobilized mice where then imaged in a posterior position with the camera preset to record 10,000 counts. No background subtraction was performed. Photographic images were obtained using Polaroid Type 330 Pack film. Two areas in each image were defined: (a) region 1, whole body; (b) region 2, tumor. FIGS. 6–8 show exemplary scintographs (also known as scintograms) produced by these experiments.

Immunoscintography imaging with intact Lym-1 was attempted at 7 days after injection and was not satisfactory, as seen in FIG. 6. FIG. 6 shows that although the tumor was visualized, the rest of the animal was also visualized. FIGS. 7 and 8 show the images of two different Raji tumor-bearing animals injected with labeled modified Lym-1 at the same time after injection. It can be seen that both FIGS. 7 and 8 show concentration of the labeled modified Lym-1 at the tumor at levels much higher than thliose at the tumor produced by the intact Lym-1, seen in FIG. 6. More importantly, the ratio of label at the tumor to the background of the whole mouse produced by the modified Lym-1 was several times higher than that of the intact Lym-1. Thus, FIGS. 7 and 8 show a clear definition of the tumor, with little or no background radioactivity.

Figure 9:
FIG. 9 shows the image obtained on day 7 after injection of I-131 labeled modified Lym-1.
Figure 10:
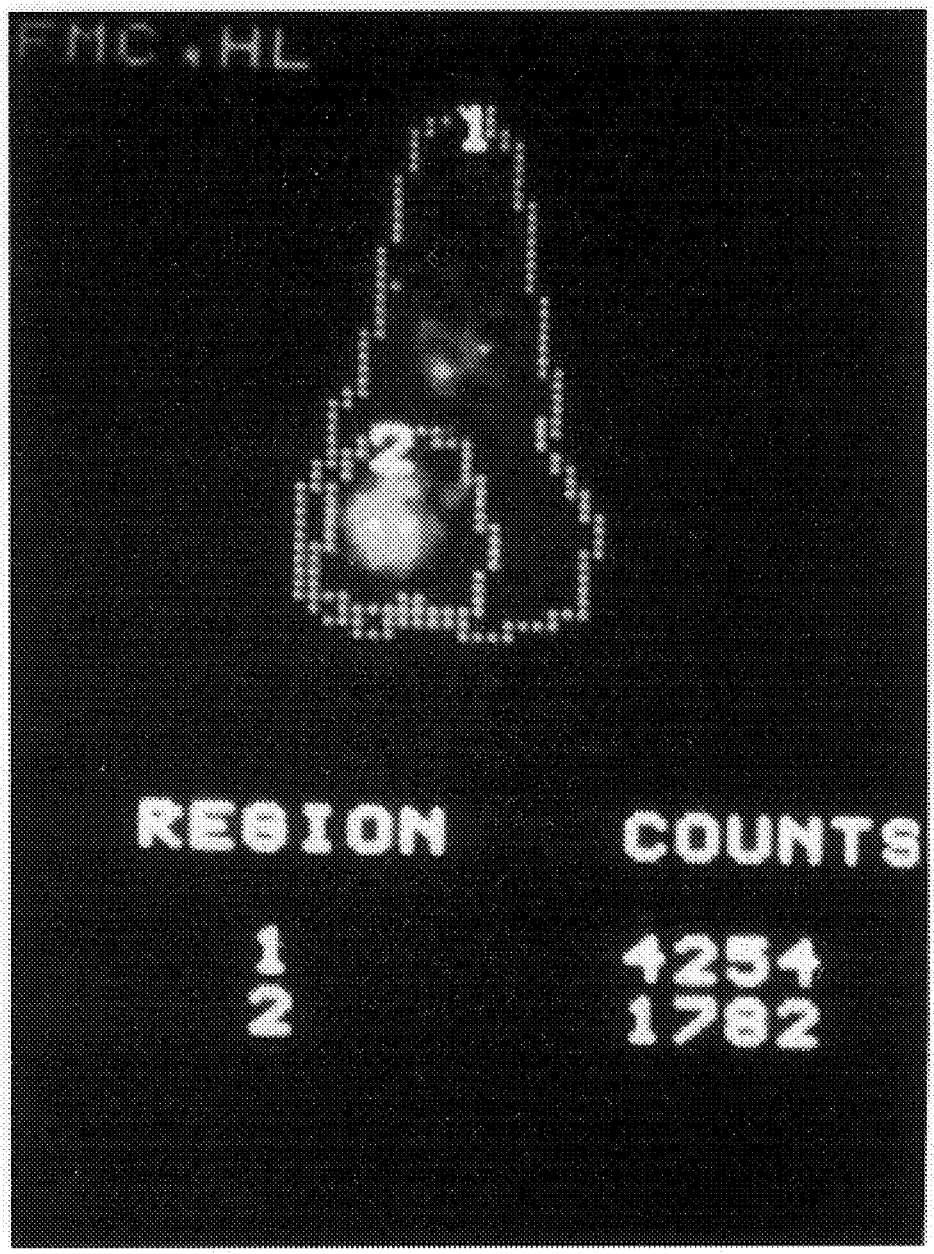
FIG. 10 shows the image obtained on day 5 after injection of I-131 labeled modified Lym-1.

Moreover, a satisfactory visualization of the tumor could be obtained at 5 days after injection when using the modified Lym-1. FIG. 10 shows a 5-day image taken of the same animal as shown in FIG. 9 at 7 days. As can be seen, the 5-day image of FIG. 10 was significantly superior to the image produced by intact Lym-1 at 7 days (FIG. 7). Results were similar for all animals tested.

This study suggests that the use of modified antibody fragments exhibit greater specific activity to tumor antigens, allowing more absolute concentration of antibody to accumulate in tumor. This is confirmed by our results that showed that the absolute concentration of modified Lym-1 fragments is about 2 times the intact Lym-1 concentration 7 days after injection and about two and a half times the F(ab')$_2$ fragments at five days.

The much faster clearance of the modified Lym-1 fragments also significantly decreases the time required to reach high tumor to background ratios and thus results in better imaging in less time than intact antibody.

In order to demonstrate the general utility of the modification of the present invention in improving the specificity and activity of antibodies, we modified additional MAb's. Tests of these various modified MAb's are shown in Examples 15–18.

EXAMPLE 15

Clearance Rate of Monoclonal Antibody B72.3

B72.3 (IgG$_1$), the monoclonal antibody against colon carcinoma, was obtained as in Coicher, D. et al, A Spectrum of Monoclonal antibodies Reactive with Human Mammary Tumor Cells, *Proc. Natl. Acad. Sci.* 78:3199–3203 (1981), the disclosure of which is hereby incorporated by reference. B72.3 MAb's were functionalized with an average of one PDP group per molecule according to the method of Example 1.

Figure 11:
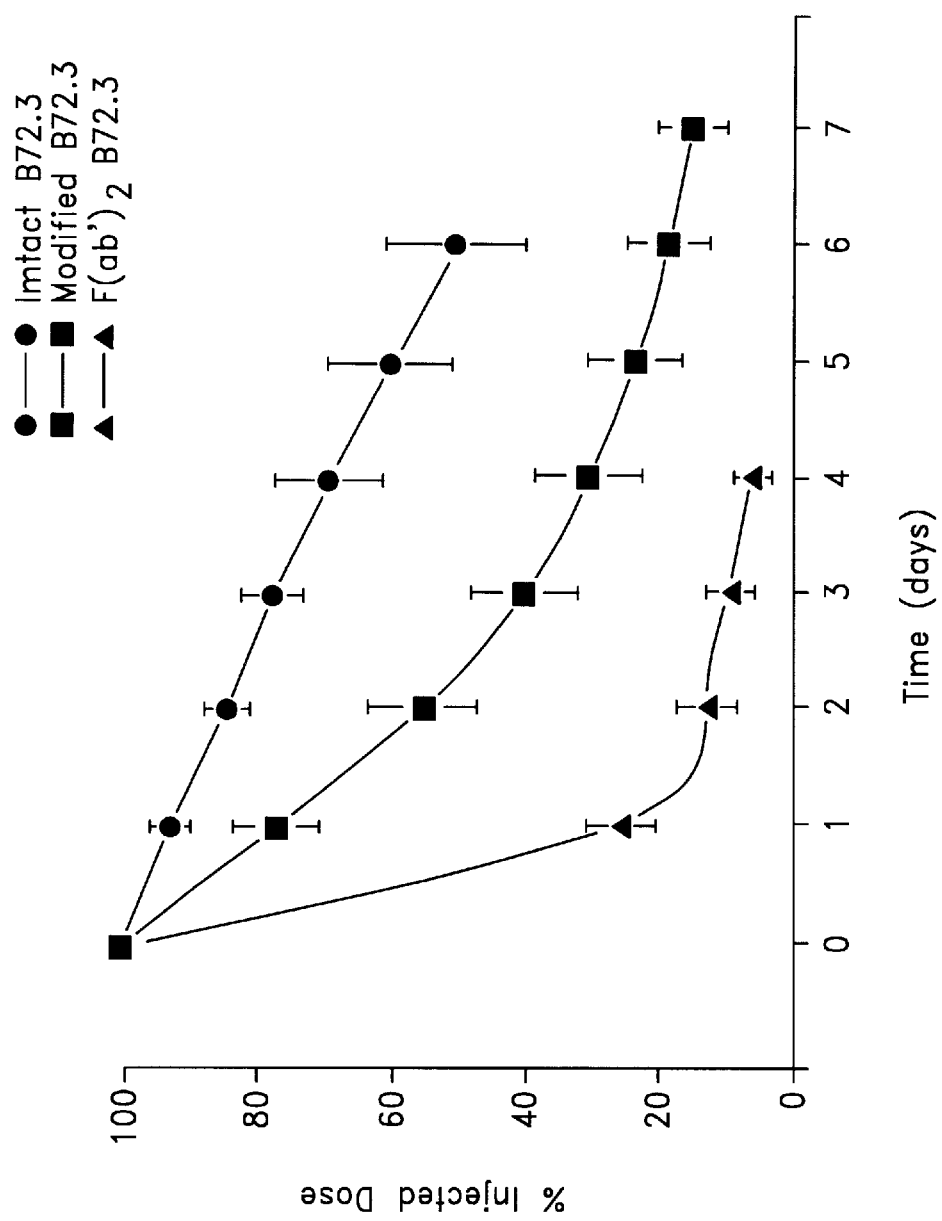
FIG. 11 shows the whole body retention of different preparations of radiolabeled monoclonal antibodies B72.3 in athymic nude mice.

The modified B72.3 MAb's were radiolabeled by the method of Example 3. Total body clearance times were measured as in Example 10. FIG. 11 shows the results of these total body clearance experiments. The modified antibodies showed a decrease in whole body half-time clearance from the approximately 6 days of intact MAb's to approximately 2.5 days for the modified antibodies. The half-time clearance of F(ab')$_2$ fragments was, as for the Lym-1 fragments, faster than the modified antibodies, with a half-time of approximately 12 hours. Thus, the results showed that modified B72.3 behaved similarly to the modified Lym-1 in having a half-time clearance intermediate between that of the F(ab')$_2$ fragments and intact antibody.

EXAMPLE 16

Biodistribution of B72.3

Figure 12:
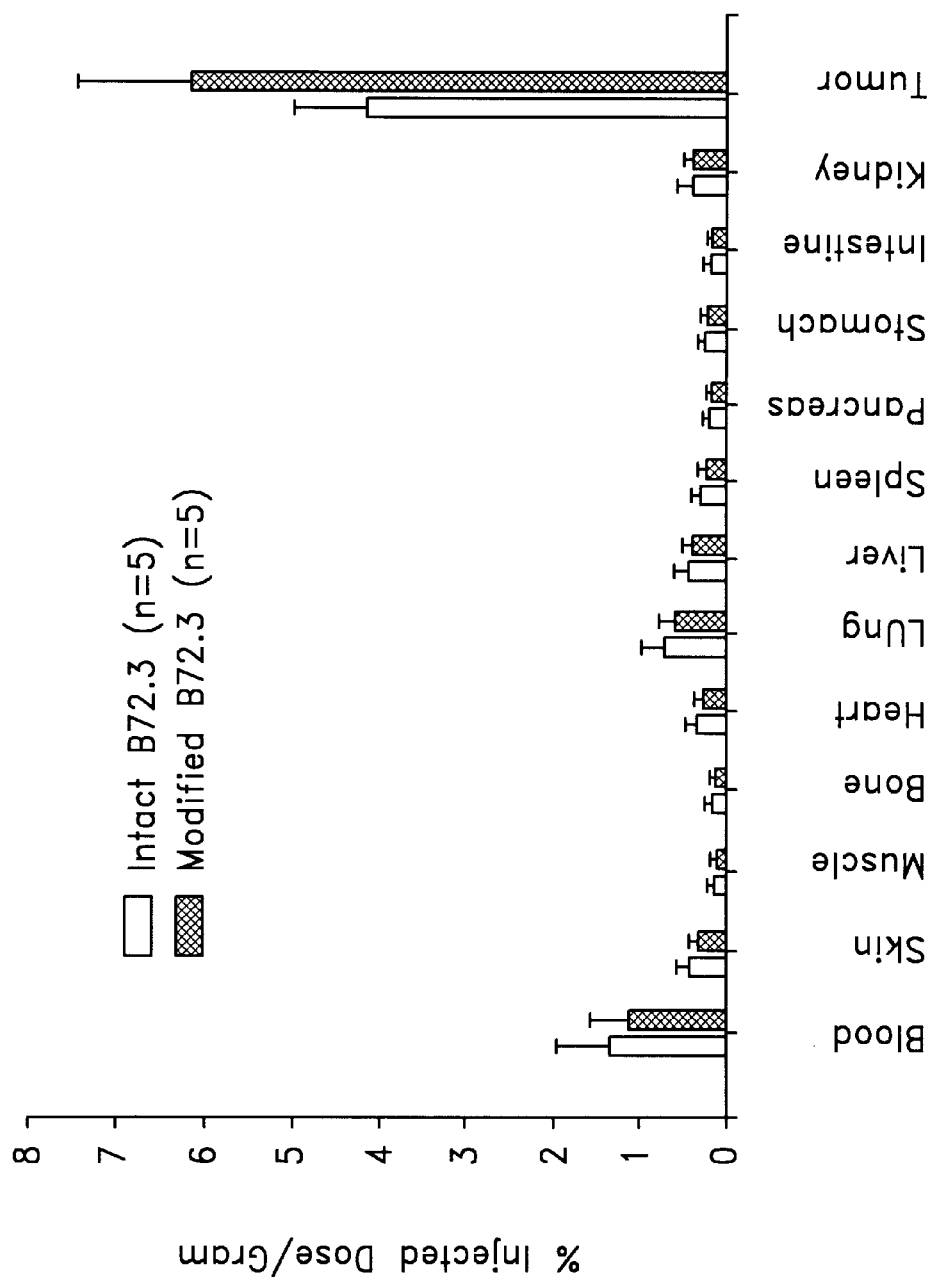
FIG. 12 shows the biodistribution as % of injected dose/gram of MAb's B72.3 and Modified B72.3 in LS174T colon carcinoma-bearing nude mice four days after injection.

Paired-label biodistribution studies for two groups of five mice each were performed in athymic nude mice bearing the human LS174T colon carcinoma. One group was injected with the intact I-125 labeled B72.3, while the other was injected with the modified I-131 labeled B72.3. The experiment also compared the biodistribution in tumor, blood and various organs. The methods employed were as in Examples 11–13. The data is reported in Table III, and shown graphically in FIGS. 11 and 12.

TABLE III

BIODISTRIBUTION OF MODIFIED AND INTACT MONOCLONAL ANTIBODY B72.3 IN THE HUMAN LS174T COLON CARCINOMA-BEARING NUDE MICE (N = 5) 4 DAYS AFTER INJECTION

| Organ | cpm/g tumor cpm/g organ | % dose/g | % dose/organ |
|---|---|---|---|
| Modified B72.3 | | | |
| Blood | 6.16(2.32)* | 1.10(0.45) | — |
| Skin | 20.81(3.92) | 0.31(0.12) | — |
| Muscle | 61.58(16.16) | 0.11(0.05) | — |
| Bone | 65.25(15.04) | 0.10(0.04) | — |
| Heart | 31.41(18.44) | 0.24(0.11) | 0.03(0.02) |
| Lung | 11.89(3.25) | 0.54(0.18) | 0.14(0.04) |
| Liver | 21.61(10.36) | 0.33(0.14) | 0.43(0.17) |
| Spleen | 37.89(15.00) | 0.18(0.09) | 0.02(0.01) |
| Pancreas | 60.23(23.73) | 0.12(0.06) | 0.02(0.01) |
| Stomach | 37.74(9.20) | 0.17(0.05) | 0.04(0.01) |
| Intestine | 68.31(28.27) | 0.10(0.04) | — |
| Kidney | 24.56(10.07) | 0.29(0.13) | 0.09(0.04) |
| Tumor | — | 6.02(1.33) | 6.45(1.53) |
| Intact B72-3 (Control) | | | |
| Blood | 3.43(1.13) | 1.34(0.60) | — |
| Skin | 10.44(1.80) | 0.41(0.15) | — |
| Muscle | 31.78(8.86) | 0.14(0.05) | — |
| Bone | 33.36(9.84) | 0.14(0.06) | — |
| Heart | 16.57(8.28) | 0.30(0.14) | 0.04(0.02) |
| Lung | 6.42(1.59) | 0.68(0.28) | 0.18(0.08) |
| Liver | 11.85(4.78) | 0.39(0.16) | 0.52(0.24) |
| Spleen | 18.94(5.61) | 0.24(0.12) | 0.02(0.01) |
| Pancreas | 29.80(9.42) | 0.15(0.05) | 0.02(0.01) |
| Stomach | 18.88(3.83) | 0.22(0.04) | 0.05(0.01) |
| Intestine | 35.61(13.48) | 0.13(0.06) | — |
| Kidney | 15.20(6.40) | 0.33(0.18) | 0.11(0.06) |
| Tumor | — | 4.04(0.84) | 4.28(0.78) |

*Mean (standard deviation).

As can be seen in Table III, intact B72.3 antibody produced a blood activity at 1.34% ID/g at 4 days after injection, and an activity of 4.04% at the tumor, as shown in Table III. Compared to intact B72.3, the modified B72.3 produced lower blood activity (1.1% ID/g) and higher tumor activity ((6.02% ID/g) at 4 days.

Figure 13:
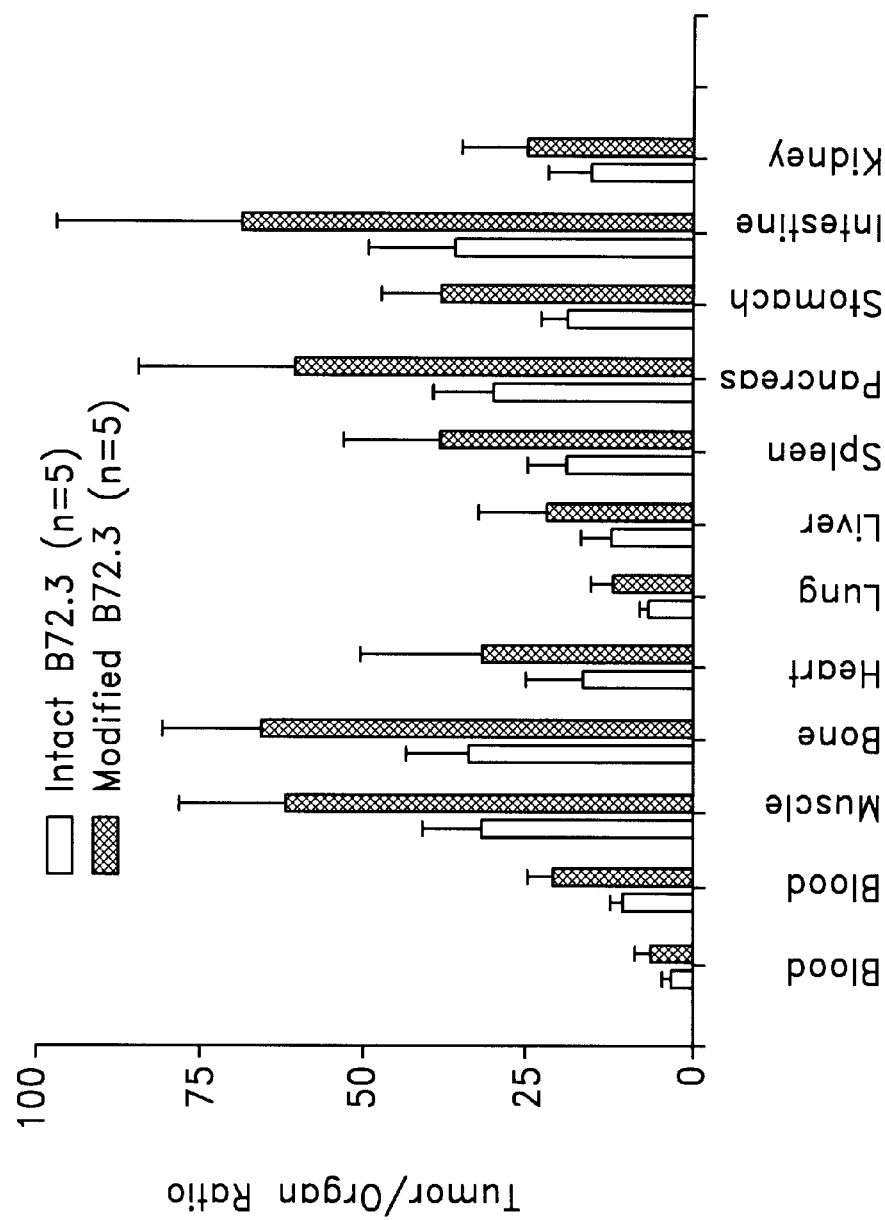
FIG. 13 shows the biodistribution as tumor/organ ratio of MAb's B72.3 and Modified B72.3 in LS174T colon carcinoma-bearing nude mice four days after injection.
Figure 14:
FIG. 14 shows the image obtained on day 1 after injection of I-131 labeled modified B72.3.

As can be seen in FIG. 13, all of the various organ activities were higher for the modified B72.3, except kidney, as expected for a more rapidly cleared antibody. Thus, as shown in FIG. 14, the tumor to organ ratio for modified B72.3 was significantly higher than the corresponding ratios for the intact B72.3. The tumor to organ ratio was even improved for kidney due to the higher activity of the modified antibody at the tumor site.

EXAMPLE 17

Imaging of B72.3 in Tumor Bearing Mice

Figure 15:
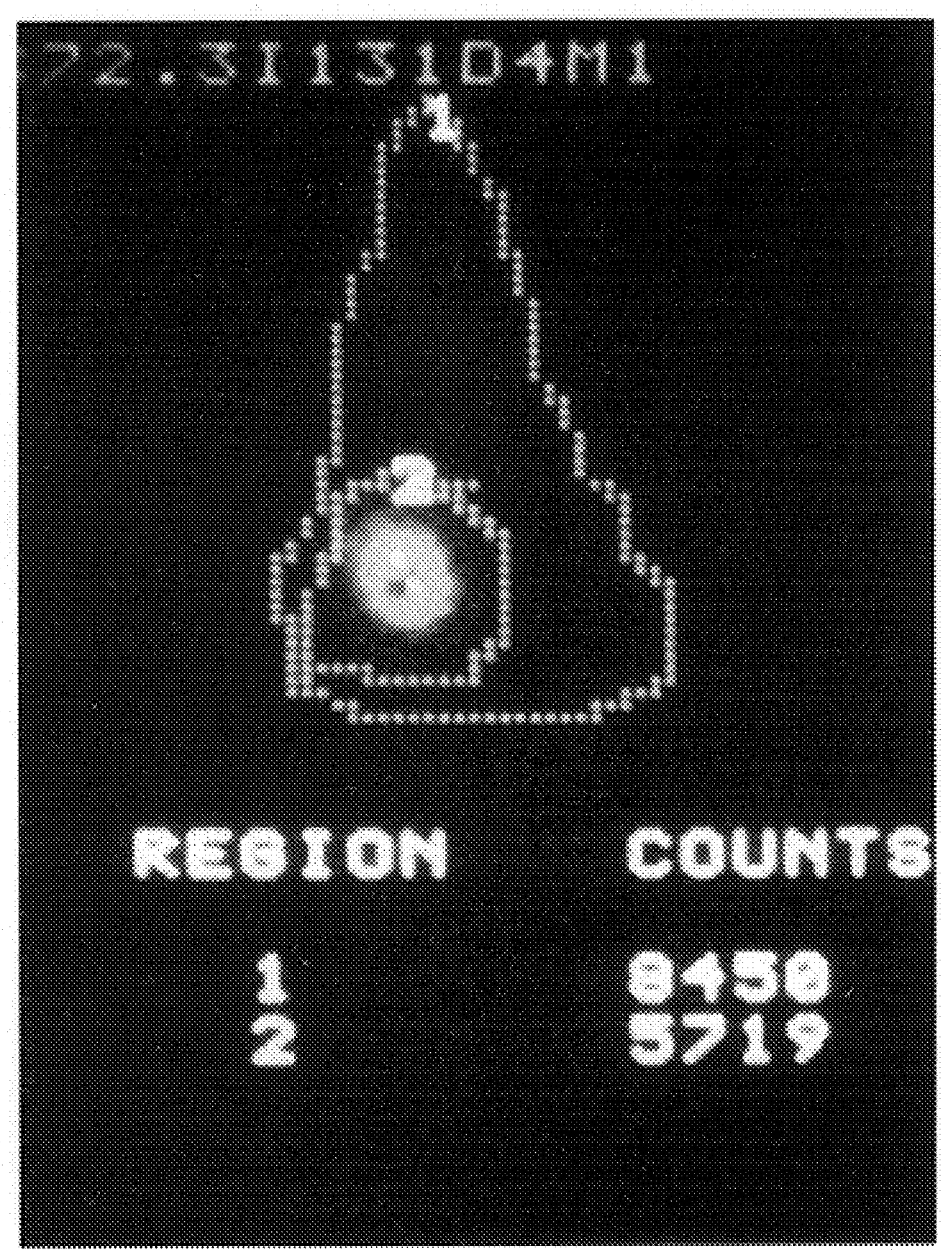
FIG. 15 shows the image obtained on day 4 after injection of I-131 labeled modified B72.3.

Image analysis of LS174T tumor-bearing mice injected with modified B72.3 provided an estimate of tumor/whole antibody distribution after injection. FIG. 14 shows an immunoscintograph at 1 day after injection. The image shows a clear definition of the tumor with little background radioactivity. FIG. 15 shows an immunoscintograph at 4 days after injection. By 4 days, the tumor was clearly seen with little radioactivity remaining in the blood pool of the animal. Results were similar for all animals.

Thus, the modified B72.3 was found to be very useful in obtaining high quality immunoscintographs within a short time of injection of tumors reactive with B72.3.

TNT-1 is an IgG$_{2a}$ monoclonal antibody which utilize necrotic tumor as a target for their selective binding to human cancers. We modified this antibody with on average one PDP group per molecule as in Example 1, and analyzed whole body retention time as shown in Example 18.

EXAMPLE 18

Use of Monoclonal Antibody TNT-1

We obtained TNT-1 as in Epstein, A. L. et al., A Novel Method for the Detection of Necrotic Lesions in Human Cancer, *Cancer Res.* 48:5842–5848 (1988), the disclosure of which is hereby incorporated by reference. The TNT-1 MAb's were radiolabeled by the method of Example 3. Total body clearance times were measured as in Example 10. FIG. 16 shows the results of these total body clearance experiments. The modified TNT-1 MAb's showed a decrease in whole body half-time clearance time relative to intact TNT-1, and an increase relative to the F(ab')$_2$ fragments of TNT-1.

Thus, the modified TNT-1 behaved similarly to the other modified antibodies. We, therefore, expect, that the utility of the modified TNT-1 MAb's to be equivalent to the other modified antibodies tested.

Example 19 describes one method useful for preparing biotinylated antibodies.

EXAMPLE 19

Preparation of Biotinylated Antibodies

The TNT-1 and Lym-1 MAb's were separately conjugated to 6-(biotinamido) hexanoate by reaction with its sulfo N-hydroxysuccinimide ester (NHS-LC-biotin). Typically, a standard solution of 2 mg NHS-LC-biotin in 1 mL of 0.9% saline solution was prepared. To a 5 mL test tube containing 1 mL of antibody (10 mg/mL) in sodium bicarbonate buffer, pH 8.5, was added 1 mL of NHS-LC-biotin standard solution (molar ratio 50:1 NHS-LC-biotin/MAb). The reagent mixture was incubated for 2.5 hours at room temperature with continuous stirring at low speed. After incubation, the coupled antibody was chromatographed on a PD-10 column (Pharmacia) equilibrated with PBS, pH 7.2. Purity of the coupled antibody preparations was assessed by FPLC using a superose-12 column. The results of these procedures indicated that the biotinylated antibody was obtained with at least 99% purity.

The average number of biotin groups coupled to each antibody molecule was determined spectrophotometrically according to the method described by Green in *Biochem J.* 94:23c-24c (1965). Briefly, the biotinylated antibody was digested enzymatically with 1% protease at 37° C. for four hours. To a 5 mL solution containing 800 μL of 100 μM HABA in 0.1 M PBS, pH 7.2 was added 70 μL of a 17 μM solution of streptavidin. The streptavidin-HABA solution was then titrated with increasing volumes of the digested biotinylated antibody solution, and the change in absorbance determined at 500 nm. From this treatment, the concentration of biotin in the protease-treated antibody solution was calculated using a standard curve of biotin solution. The results indicated that an average of from 3 to 4 biotin moieties were incorporated into each antibody molecule.

The biotin-antibody conjugates were radiolabeled with $^{125}$I using the chloramine-T method essentially as described in Example 3.

Example 20 describes the methods used for radioiodination of antibodies and antibody fragments.

EXAMPLE 20

Direct Radioiodination of Antibodies

All antibodies (intact, modified, and F(ab')$_2$ fragments) were iodinated with $^{125}$I or $^{131}$I using a modified chloramine-T method essentially as described in Example 3. Typically, 0.5–1.0 mCi of iodine-125 or iodine-131 and 10 μL of a 43 mM aqueous solution of chloramine-T were added to a test tube containing 50–100 μg of the monoclonal antibody in 100 μL PBS. The reaction was quenched after three minutes with 20 μL of a 120 mM solution of sodium metabisulfite. The radiolabeled antibodies were purified using a Sephadex G-25 column. This column consisted of a serological plastic pipette (8×200 mm) plugged at the end with cotton ($V_o$=4.5 mL, $V_t$=12 mL). Each reaction mixture was loaded onto a column and eluted with PBS, pH 7.2. Individual tubes containing 1 mL aliquots were counted in a scintillation counter. Radiolabeled antibodies were typically recovered with 85–90% yield. All antibodies radiolabeled by the chloramine-T method were analyzed using an analytical instant thin layer chromatography (ITLC) system on silica gel impregnated glass fibers. Strips (2×20 cm) were activated by heating at 110° C. for 15 minutes prior to use, spotted with 1 μL of sample, air dried, and eluted with methanol/H$_2$O (80:20) for approximately 12 cm, again air dried, cut in half and counted to determine protein bound and non-protein bound radioactivity. Results of this procedure indicated that greater than 99% of the antibody was protein bound, thereby confirming that functional radiolabeled biotinylated antibodies could be obtained with high purity.

The radiolabeled biotinylated antibodies prepared according to the procedure described above were stored at 4° C. and administered to mice within four hours of labeling.

The following two Examples disclose the results of analytical procedures used to prove that radiolabeled biotinylated antibodies retained the ability to bind target antigens and were stable in the presence of serum constituents.

Example 21 describes the methods used to demonstrate that antibodies having been modified by biotinylation and radiolabeling retained both antigen-binding ability and structural integrity.

EXAMPLE 21

Immunoreactivity assessment

The in vitro immunoreactivities of radiolabeled Lym-1 preparations were evaluated with a live cell assay using Raji cells according to the method described by Epstein et al. in *Cancer Res.*, 47:830 (1987). Raji cells (10$^6$/test tube) were resuspended in 100 μL of 1% bovine serum albumin (BSA) in PBS. Labeled Lym-1 (100 μl) was added to each test tube (approximately 10 μCi/lg; 100,000 cpm/tube) in triplicate and incubated for one hour at room temperature with continuous mixing using an orbital shaker. After incubation, the cells were washed three times with 1% BSA in PBS by centrifuging the tubes at 1000 rpm for five minutes, decanting the supernatant, and resuspending the cells in 200 μL PBS. Following completion of the washes, bound Lym-1 was detected by measuring the cell pellet-associated radioactivity using a gamma counter. The results of this procedure were substantially identical to those presented under Example 6. More specifically, 75% of radiolabeled intact Lym-1 and 75% of radiolabeled biotinylated Lym-1 bound the target cells. This indicated that the antigen binding activity of radiolabeled biotinylated Lym-1 was comparable to that of the radiolabeled intact Lym-1 which served as a standard control.

Immunoreactivity of the modified TNT-1 MAb was evaluated using a fixed cell radioimmunoassay described by Gaffar et al. in *J. Immunoassay*, 2:11 (1991). Briefly, radiolabeled TNT-1 and radiolabeled biotinylated TNT-1 were incubated for 30 minutes with Raji cells previously fixed with 20% paraformaldehyde in PBS at room temperature and then treated with acetone at −20° C. The cells were then washed with 1% BSA in PBS and counted in a gamma counter. The results of this procedure indicated that approximately 60% of both antibody preparations bound to the fixed cells. This indicated that the antigen binding activity of radiolabeled biotinylated TNT-1 was comparable to that of the radiolabeled intact TNT-1 which served as a standard control.

Example 22 describes the methods used to prove that radiolabeled biotinylated antibodies were not unusually subject to degradation in the presence of serum.

EXAMPLE 22

Serum Stability of Modified Antibodies

MAb's labeled directly with $^{125}$I were added to a triplicate set of tubes containing fresh mouse serum to a final concentration of 100 μg/mL. All samples were incubated at 37° C. in a humidified incubator maintained at 5% CO$_2$ in air. At various times between 0 and 8 days, protein-bound radiolabel was determined by adding 900 μL of 100% trichloracetic acid (TCA) to 100 μL aliquots of each sample, incubating at room temperature for five minutes and recovering protein precipitates by centrifugation. Aliquots (500 μl) of supernatant were withdrawn from each tube and counted for radioactivity using a gamma counter. The results indicated that radiolabeled biotinylated antibody was stable in vitro at all time points. More specifically, at least 97% of the radiolabel remained protein-associated after 8 days of incubation. This confirmed that the biotin moieties present on the MAb's had no detrimental effect on the stability of the protein-associated radiolabel.

The same aliquots of each incubated serum mixture were also serially checked by non-reducing SDS-PAGE and autoradiography. For this study, samples were electrophoresed on 10% polyacrylamide gels and visualized by exposure to X-ray film. Molecular weights of the samples were determined by comparison to molecular weight standards. The results of these procedures indicated that radiolabeled intact MAb and the radiolabeled biotinylated MAb had substantially similar molecular weights. More specifically, the major bands for radiolabeled Lym-1 and radiolabeled biotinulated Lym-1 had $M_r$s of approximately 200,000. Similarly, the major bands for radiolabeled TNT-1 and radiolabeled biotinulated TNT-1 had $M_r$s of approximately 150,000.

Isoelectric focusing in polyacrylamide gels was performed in a BioRad Model 111 Mini IEF cell. Samples were electrophoresed through a pH gradient constructed with a mixture of BioLyte ampholytes (BioRad) at concentrations of 1.2% 3/10 ampholyte and 0.8% 5/8 ampholyte according to protocols provided by BioRad. IEF standards (BioRad) were included in each run for calibration of pI. IEF gels were stained with Coomassie Blue R-250 and dried overnight. The results of these procedures confirmed that biotinylation of the MAb's substantially altered the electrical charge properties of the macromolecules. While the radiolabeled Lym-1 had a pI value of 7–8, the radiolabeled biotinylated Lym-1 had a pI of 5–6. Similarly, while the radiolabeled TNT-1 MAb had a pI value of 5.5–6.5, the radiolabeled biotinylated TNT-1 MAb had a pI of 4.5–5.0. Thus, as expected, modification of free amino groups on the MAb protein effectively eliminated or neutralized some of the positive charge on the proteins as evidenced by the less basic character of the biotinylated antibodies.

Example 23 describes the methods used to demonstrate that MAb's having aminoside moieties chemically modified to result in a macromolecule having reduced pI relative to native antibody advantageously exhibited: (1) increased target specificity, (2) decreased non-specific binding and (3) decreased clearance time.

EXAMPLE 23

Biodistribution Studies

Two groups of six-week-old nude mice were injected with either Raji lymphoma cells, LS-174T colon carcinoma cells, or ME-180 cervical carcinoma cells according to the methods described by Khawli et al. in *Antibody, Immunoconjugates, and Radiopharmaceuticals* 6:13 (1993). The tumors were grown for 10–21 days until they were approximately 1 cm in diameter.

(a) Paired-label studies. In the first group of mice (n=6), each mouse was injected intravenously with a 0.2 mL inoculum containing 120 $\mu$Ci/10 $\mu$g of modified $^{131}$I-labeled MAb and 25 $\mu$Ci/10 $\mu$g of intact I$^{125}$I-labeled MAb. In the second group (n=4), mice received a 0.2 mL inoculum containing 120 $\mu$Ci/10 $\mu$g of modified $^{131}$I-labeled MAb and 25 $\mu$Ci/10 $\mu$g of $^{125}$I-labeled MAb F(ab')$_2$. In all experiments, mice were sacrificed by cervical dislocation at preselected times post-injection and various organs, blood, and tumor were removed and weighed. The samples were then counted in a gamma counter to quantitate the $^{131}$I and $^{125}$I activities. $^{125}$I counts were adjusted for crossover from the $^{131}$I channel by subtracting 17% of the $^{131}$I channel counts, a formula that was determined experimentally for the 1282 CompuGamma counter. The data were also corrected for the radiation decay of the $^{131}$I isotope according to the time when the animals were sacrificed. For each mouse, data are expressed as cpm per gram tumor/cpm per gram organ and % dose/gram. From these data, the mean and standard deviation were calculated for each group. The same paired-label biodistribution studies were performed using Lym-1 in the Raji lymphoma model and B72.3 in the LS-174T human colon carcinoma model.

Figure 17A:
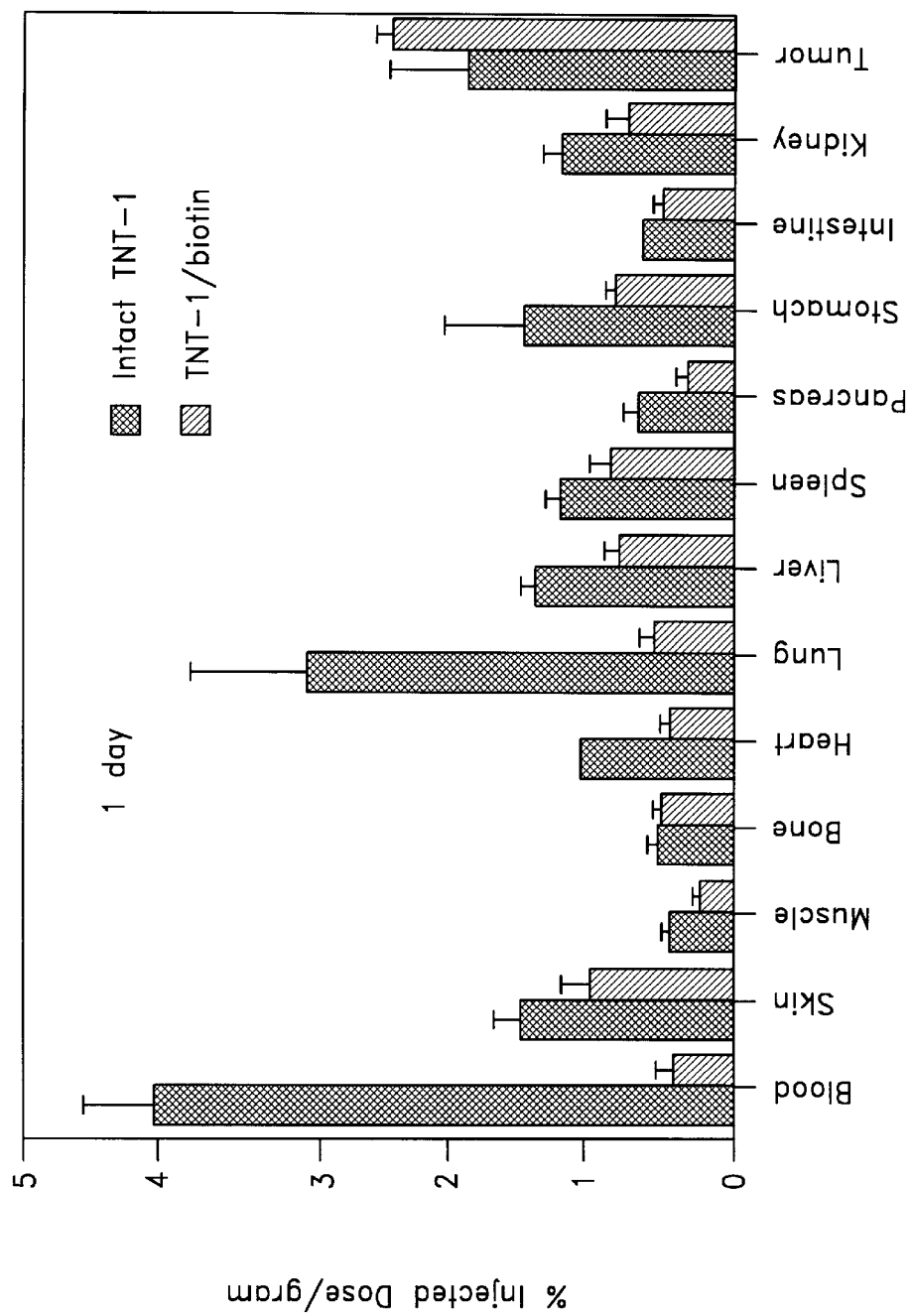
Figure 17B:
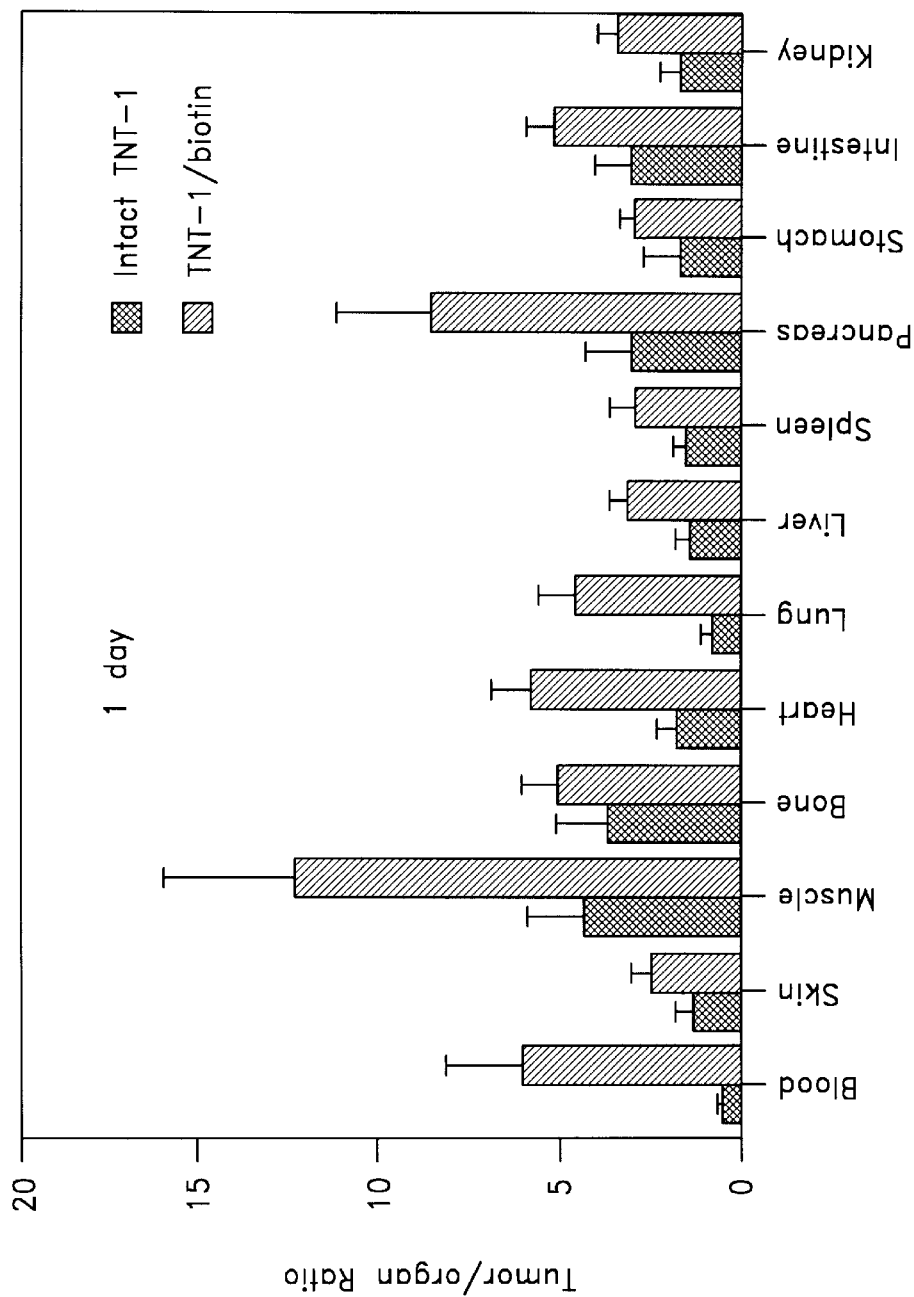

The results of these procedures are presented in FIG. 17. As indicated in panel 17A, while both intact TNT-1 and TNT-1/biotin modified MAb's localized to tumor tissue at one day post-injection, the biotinylated antibody exhibited a greater localization as measured by the % injected dose/gram of tumor. Non-specific binding of the two labeled MAb's was also evident in a variety of tissues. Importantly, the amount of biotinylated TNT-1 that non-specifically associated with these tissues was uniformly less than the amount of intact TNT-1 that exhibited such non-specific binding. Thus, the level of specific binding was elevated and the level of non-specific binding was decreased for the biotinylated antibody relative to the unmodified antibody. The advantage of the modified antibody is represented quantitatively in FIG. 17B, wherein the ratio of tumor-localized antibody to non-specifically localized antibody is presented for each tissue. As illustrated, the advantage of the biotinylated antibody as an imaging reagent was particularly evident in muscle and pancreas.

Figure 17D:
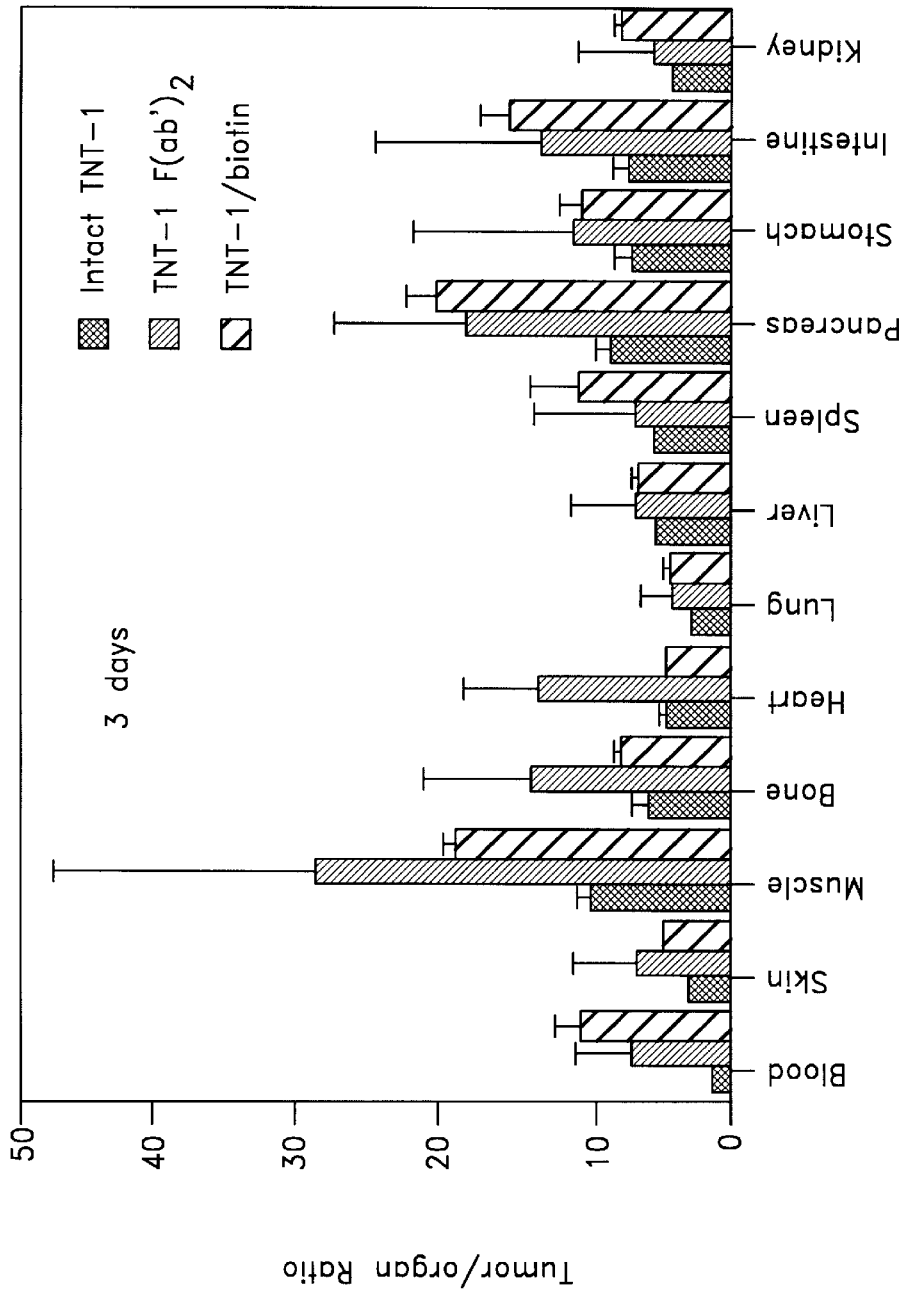

Similar trends were observed for measurements taken at three days post-injection. FIG. 17C shows that biotinylated TNT-1 antibody localized to tumor tissue more efficiently than the non-biotinylated counterpart antibody. At the same time, the amount of non-specific binding was advantageously lower for the biotinylated species. FIG. 17D quantitatively confirms that the tumor/organ ratio, which reflects the signal-to-noise ratio in various tissues, was highest in muscle and pancreas. Notably, FIGS. 17C and 17D include results obtained using TNT-1 F(ab')$_2$ fragments which have rapid whole-body clearance rates. Although the tumor/organ ratio was higher for the antibody fragments compared to biotinylated TNT-1 in several tissue types, the fraction of injected biotinylated TNT-1 that localized to tumor was advantageously higher. These results illustrated that a biotinylated MAb localized to tumor tissue in a fashion that was superior to either unmodified intact MAb, or F(ab')$_2$ MAb fragments.

(b) Whole-body clearance. Experiments were performed in which different groups of Balb/c mice (n=45) were given i.v. injections of radiolabeled antibodies. The whole-body activity at injection and at selected times thereafter was measured with a dose calibrator.

Figure 18:
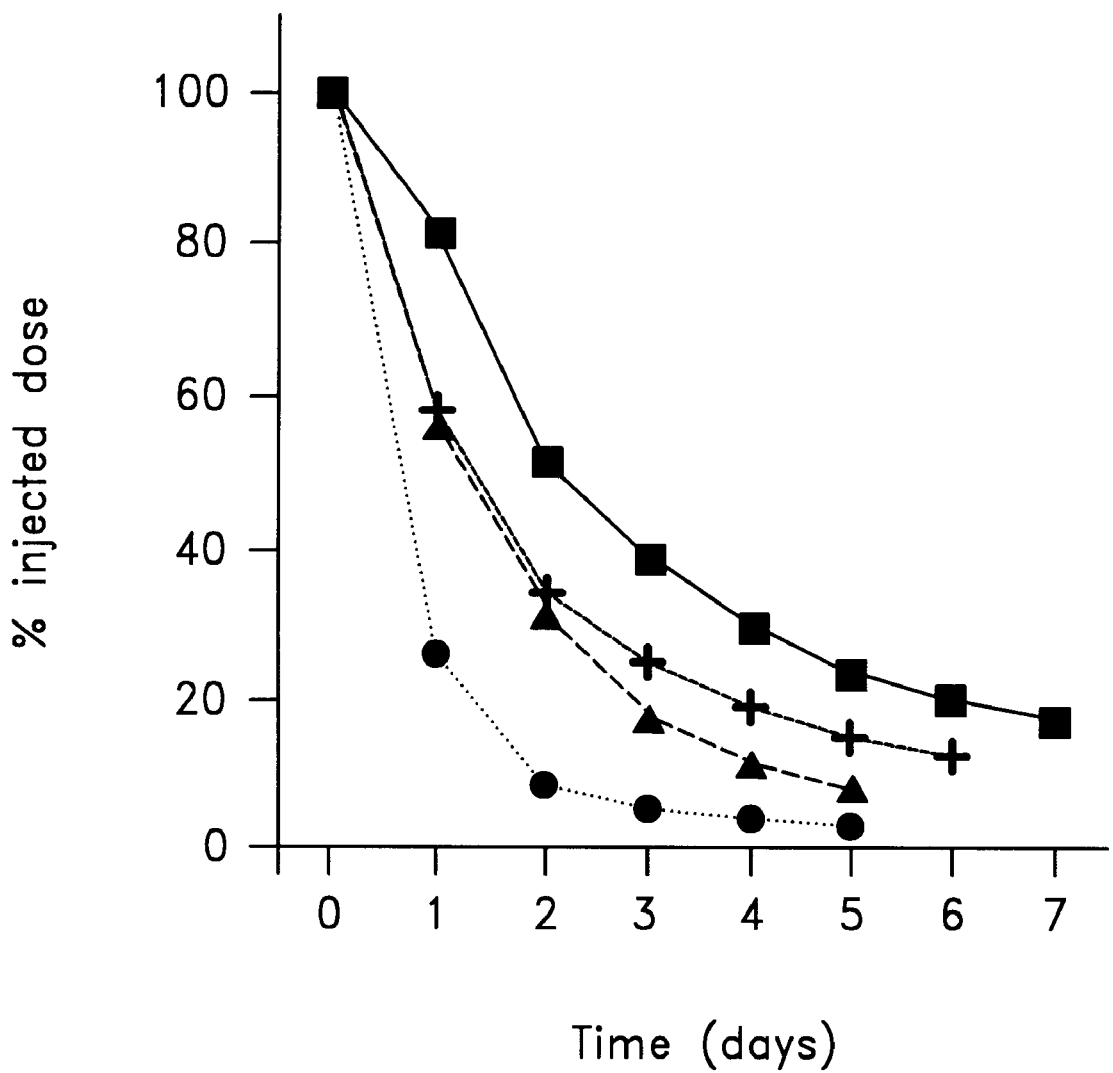
FIG. 18 shows a line graph representing whole-body clearance of intact TNT-1, modified TNT-1 and F(ab')$_2$ fragments in Balb/c mice.
Figure 19:
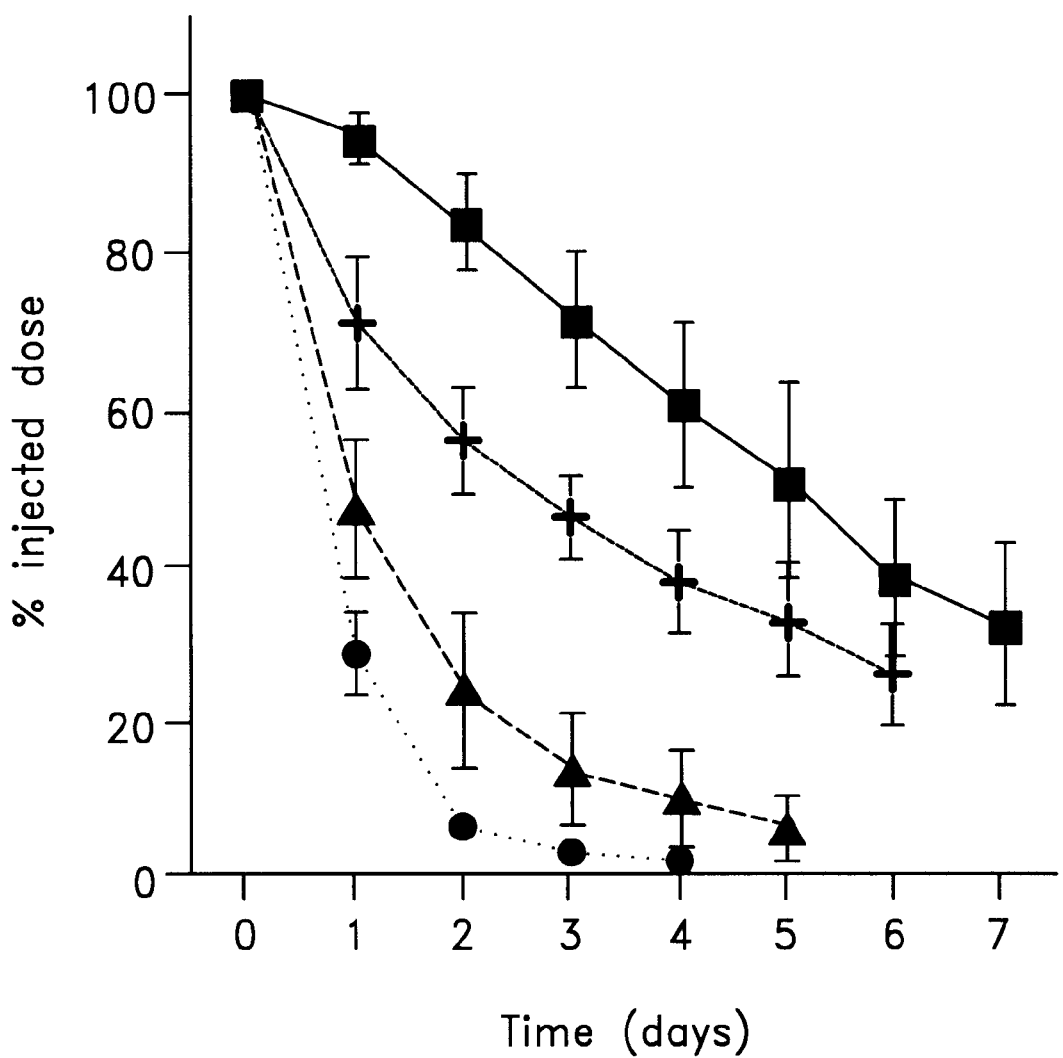
FIG. 19 shows a line graph representing whole-body clearance of intact Lym-1, modified Lym-1 and F(ab')$_2$ fragments in Balb/c mice.

FIGS. 18 and 19 disclose the results of whole-body clearance rate studies for TNT-1 and Lym-1 antibodies and their derivatives. The results presented in FIG. 18 indicated that TNT-1 MAb modified by either SPDP or biotin have decreased clearance times relative to the intact antibody. The F(ab')$_2$ TNT-1 fragment, which had the fastest clearance rate of all antibodies tested was used as a positive control in this procedure. Thus, the biotinylated TNT-1 MAb advantageously exhibited a more rapid clearance rate than the non-biotinylated antibody. Similarly, the results presented in FIG. 19 indicated that Lym-1 MAb modified by either SPDP or biotin had decreased clearance times relative to the intact antibody. This illustrated that agents that chemically modified free amino groups moieties to reduce the pI of the antibody advantageously increased the antibody binding specificity and whole-body clearance rate.

We believe that modifications to any antibody using the methods of the present invention will provide a reagent useful for improved tumor imaging. In order to produce an image of any desired tissue type using the methods of the present invention, antibodies to that tissue type must first be obtained. Polyclonal antibodies can be obtained in a conventional manner as will be known by one of skill in the art. Alternatively, monoclonal antibodies can be prepared in order to obtain the increased specificity provided by these antibodies, as will also be known by one of skill in the art. The antibodies are then chemically modified at free amino groups by conjugation with a heterobifunctional agent, biotin, or other agent that will lead to a modified antibody product having an isoelectric point that is lower than the isoelectric point of the unmodified antibody. After conjugation, a suitable label is applied to the modified antibodies.

Although the foregoing Examples make use of imaging of a label comprising a gamma radiation emitting radionuclide, many other label types and imaging systems are contemplated within the scope of the present invention. For example, radio-opaque materials, such as barium, cesium or iodine can be imaged using conventional X-rays. Paramagnetic or supermagnetic particles can be used as labels, using MRI imaging technology to produce an image of the location of the antibodies. Additionally, technicium can be used as label. These alternative labels may be conjugated to the modified antibodies using conventional methods.

The labeled antibodies can be included in pharmaceutical preparations for the introduction of label into a subject including pharmaceutically acceptable excipients, carriers, or bases. Suitable excipients, carriers, or bases include saline, phosphate buffered saline, glycerol, calcium carbonate, and the like. These compositions are then introduced through any of a variety of means, such as local injection, intravenous injection, or oral administration in cases where reduced signal strength is required or where imaging of tissue in the oral cavity are desired. However, preferably, administration is through systemic injection in order to maximize exposure of the targeted tissue to the antibody.

We believe that chemical modification of free amino groups disposed on antibodies by addition of a heterobifunctional agent, biotin or other agent to result in a modified antibody having a lower isoelectric point than a corresponding unmodified intact antibody in accordance with the present invention will produce significantly improved results when these modified antibodies are incorporated into an immunotherapeutic agent. Such therapeutic agents generally comprise an antibody specific to a tumor or other diseased tissue combined with one or more biologically active molecules. Suitable biologically active molecules which function in such agents are toxins, such as the diphtheria toxin (ricin) A-chain or any of a variety of plant toxins known by those of skill in the art; radionuclides, such as radioactive isotopes of yttrium, iodine, phosphorus, and other commonly used radio-therapeutic agents; drugs, such as methotrexate, 5-fluoro-uracil, or adriamycin; chelates, including EDTA and EGTA; cis-platinum and other toxic organo-metallic agents, and any other therapeutic agent.

Heretofore, the promise of effective immunotherapy has yet to be fully realized. We believe that the increased activity and specificity of the modified antibodies of the present invention will produce immunotherapeutic agents having sufficient activity and specificity for their target tissues to overcome the deficiencies of prior immunotherapeutic agents. Thus, target disease tissues can be killed without significantly affecting the healthy tissues of the subject, when the subject is injected with the appropriate immunotherapeutic agent.

In the use of these immunotherapeutic agents, antibodies specific to particular undesired tissue types must first be obtained. If the desired antibodies are not available, the antibodies may be raised in a suitable organism by injecting the organism with antigens and obtaining serum from the mammal, as will be known by one of skill in the art. Alternatively, and preferably, monoclonal antibodies can be raised in a manner known to one of skill in the art. The antibodies are then chemically conjugated with an agent such as a heterobifunctional agent, biotin or other agent capable of modifying free amino groups present on the antibody molecule. After conjugation, the resulting modified antibodies are further modified by conjugation with a biologically active agent, such as a therapeutic agent or detectable label as described above. The antibodies are combined into pharmaceutical compositions containing a pharmaceutically acceptable carrier, excipient or base. Such pharmaceutically acceptable carriers, excipients, or bases include normal saline for systemic injection, glycerol, calcium carbonate. The compositions are then ready for introduction into a patient, such as a mammal.

The antibodies are then introduced into the subject via any known administration route. For example, the compositions can be introduced through systemic injection, local injection into the affected tissue, can be applied topically to externally affected tissue, and can be taken orally in cases where reduced signal strength is required or where therapy of tissue in the oral cavity are desired.

Dosage of the biologically active agent containing antibody will depend on target tissue sensitivity to the toxin, the amount of affected tissue, route of administration, the affinity of the antibody, clearance rates and on other factors. However, representative dosages will generally be in the range from 1 $\mu$g/kg total body mass to 1 mg/kg. In most applications, the dose will preferably be from 5 to 200 $\mu$g/kg.

The following Example is illustrative of an immunotherapy effective against Raji tumors in mice. Although PDP-modified antibodies are employed in the Example, antibodies having free amino groups modified by other agents, such as biotin, that will produce a modified antibody having a pI lower than a corresponding intact antibody are expected to work equally well.

EXAMPLE 24

Treatment of Raji Tumors in Mice

PDP-modified Lym-1 is obtained as in Example 1. The modified antibody is then treated to introduce, on average, one ricin A-chain per antibody molecule. Intact Lym-1 and F(ab')$_2$ fragments are similarly combined with toxin.

Twenty-five mice are divided into five groups. Group I receives intraperitoneal injections at 10 $\mu$g/kg total body weight of the ricin-PDP-modified Lym-1 in phosphate buffered saline (PBS) once per week for 8 weeks. Group II receives injections of an equivalent amount ricin-intact Lym-1. Group III receives equivalent amounts of ricin-F(ab')$_2$ fragments of Lym-1. Group IV receives an equivalent amount of unconjugated ricin. Group V receives PBS alone.

After 8 weeks, immunoscintography of all surviving mice using the method of Example 14 is performed. The Group I mice show reduced visualization of tumor compared to any of the other groups. Surviving Group II and Group III mice show some improvement, though less dramatic than the Group I mice. Group IV mice become very ill or die.

Thus, Example 24 shows one particular treatment of a tumor using the modified antibodies of the present invention. Example 19 shows the superior results achieved when using the PDP-modified antibodies of the present invention. Substituting the use of other antibodies specific to other tumors or diseased tissues in mice or other mammals, such as humans, is believed to produce similarly effective results in treating those specific tumors or diseased tissues. Moreover, the substitution of other know toxins is believed to also produce similarly effective results. Example 20 shows the use of a similar therapy effective against pancreatic cancer in humans. Although PDP-modified antibodies are employed in the Example, antibodies having free amino groups modified by other agents, such as biotin, that will produce a modified antibody having a pI lower than a corresponding intact antibody are expected to work equally well.

EXAMPLE 25

Treatment of Human Pancreatic Cancer

A monoclonal antibody is obtained which is specific to an antigen found in human pancreatic tumors. This antibody is modified by conjugation to, on average, one PDP group per antibody molecule, as in Example 1. Methotrexate is then conjugated to these modified antibodies as described for Ricin in Example 19.

Two groups of ten pancreatic cancer patients are treated. The first group receives intravenous injections of the drug-PDP-MAb in PBS at 20 μg/kg total body weight on a weekly basis in combination with traditional therapy. The second, group receives injections of PBS in combination with traditional therapy as a control. After 10 weeks, immunoscintography of the surviving patients is performed.

On immunoscintography, the average size of the tumors imaged in the first group of patients is reduced relative to the control group.

Thus, the foregoing example illustrates the utility of the modified antibodies in immunotherapy in humans.

As described above, in one preferred form of the present invention, the modified antibodies are formulated into pharmaceutical compositions. Thus, the PDP-modified antibodies which are conjugated with a drug for immunotherapy may be incorporated into an injectable composition having a cytotoxicity effective amount of the modified antibody-toxin conjugates of the present invention. The following is an-example of a cytotoxicity effective composition effective against B-cell lymphomas in humans.

EXAMPLE 26

A Pharmaceutical Composition Effective Against B-Cell Lymphoma in Humans

| | |
|---|---|
| 10 mg/mL | Modified radiolabeled Lym-1 from Example 18 |
| Balance | Phosphate Buffered Saline (0.9%) |

Additionally, the radiolabeled modified MAb's may be formulated into compositions effective to visualize their specific antigens in immunoscintography. The following is one example of such a composition.

EXAMPLE 27

A Pharmaceutical Composition Effective in Immunoscintography of Colon Carcinoma

| | |
|---|---|
| 10 mg/mL | Modified radiolabeled B72.3 from Example 15 |
| Balance | Phosphate Buffered Saline (0.9%). |

Although the Example 23 illustrated one method for localizing radiolabeled biotinylated antibodies, those having ordinary skill in the art will appreciate that alternative methods for localizing labeled antibodies will also be applicable. For example, the distribution of radioiodinated biotinylated antibodies can be localized by immunoscintographic imaging exactly as described in Example 14. Thus, for example, radioiodinated biotinylated MAb having binding specificity for a tumor antigen would be useful in diagnostic procedures. The following Example describes how such an imaging procedure could be carried out.

Example 28 describes one method wherein radiolabeled biotinylated MAb's can be used to image tumor cells in vivo.

EXAMPLE 28

Imaging of Melanoma Tumor Cells

A human patient having been diagnosed with metastatic melanoma is first identified. Immunohistological analysis indicates that the patient's melanoma expresses a cell surface antigen stainable with an anti-melanoma MAb. The anti-melanoma MAb is first chemically modified by biotinylation of free amino groups according to the method of Example 19 and radioiodinated with $^{131}$I according to the method of Example 20. Substantially purified radiolabeled biotinylated anti-melanoma MAb is then combined with a pharmaceutically acceptable excipient and administered to the patient. After three days, the injected modified MAb's have substantially localized to cells expressing melanoma antigens. The localized MAb's are then visualized by immunoscintographic imaging using a pinhole collimator and a spectrum 91 gamma camera obtainable from Raytheon. The photographic record indicates a small area of radioactivity on the patients skin, thereby identifying a secondary tumor.

It will be appreciated that certain mechanical or chemical variations may suggest themselves to those skilled in the art. The foregoing examples and detailed description are to be clearly understood as given by way of illustration, the spirit and scope of this invention being limited solely by the appended claims.

We claim:

1. A composition of matter, comprising:
   an antibody conjugated to biotin at at least one of a plurality of free amino groups disposed on the antibody to produce a modified antibody, said antibody having a reduced net positive charge compared to intact antibody, said antibody having an in vivo clearance rate between the clearance rates of F(ab')$_2$ fragments and intact antibodies of the same type with the proviso that said biotin is not bound to said antibody through a heterobifunctional agent; and
   a chemical moiety attached to the modified antibody.

2. The composition of claim 1, wherein said antibody is selected from the group consisting of monoclonal antibody and a polyclonal antibody.

3. The composition of claim 1, wherein the chemical moiety is a label.

4. The composition of claim 3, wherein the label is a radionuclide.

5. The composition of claim 4, wherein the radionuclide is selected from the group consisting of a halogen radionuclide and Technicium.

6. The composition of claim 5, wherein said halogen radionuclide is selected from the group consisting of $^{125}$I and $^{131}$I.

7. The composition of claim 3, wherein said label is detectable by magnetic resonance imaging.

8. The composition of claim 1, wherein the chemical moiety is a biologically active molecule.

9. The composition of claim 8, wherein said biologically active molecule is selected from the group consisting of a toxin, a drug and a chelate.

10. The composition of claim 9, wherein said drug is selected from the group consisting of methotrexate, 5-fluoro-uracil, cis-platinum and adriamycin.

11. A composition of matter, comprising:

an antibody conjugated to a chemical reagent at at least one of a plurality of free amino groups disposed on the antibody to produce a modified antibody, said antibody having a reduced net positive charge compared to intact antibody, said antibody having an in vivo clearance rate between the clearance rates of the $F(ab')_2$ fragments and intact antibodies of the same type, with the proviso that said chemical reagent is not a heterobifunctional agent; and a chemical moiety attached to the modified antibody, wherein said chemical moiety comprises ricin A-chain.

* * * * *

UNITED STATES PATENT AND TRADEMARK OFFICE
CERTIFICATE OF CORRECTION

PATENT NO.   : 5,990,286
DATED        : November 23, 1999
INVENTOR(S)  : Khawli et al.

It is certified that error appears in the above-identified patent and that said Letters Patent is hereby corrected as shown below:

Column 26,
Line 52, please change "of monoclonal" to -- of a monoclonal --.

Signed and Sealed this

Tenth Day of June, 2003

JAMES E. ROGAN
*Director of the United States Patent and Trademark Office*